United States Patent
Costa et al.

(10) Patent No.: US 12,360,123 B2
(45) Date of Patent: Jul. 15, 2025

(54) E3 UBIQUITIN LIGASE (UBE3A) PROTEIN TARGETS

(71) Applicant: Hoffmann-La Roche Inc., Little Falls, NJ (US)

(72) Inventors: Veronica Costa, Basel (CH); Thomas Peter John Dunkley, Basel (CH); Nikhil Janak Pandya, Basel (CH); Ravi Jagasia, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 923 days.

(21) Appl. No.: 17/423,359

(22) PCT Filed: Jan. 15, 2020

(86) PCT No.: PCT/EP2020/050861
§ 371 (c)(1),
(2) Date: Jul. 15, 2021

(87) PCT Pub. No.: WO2020/148310
PCT Pub. Date: Jul. 23, 2020

(65) Prior Publication Data
US 2022/0091137 A1    Mar. 24, 2022

(30) Foreign Application Priority Data
Jan. 17, 2019 (EP) .................................. 19152337

(51) Int. Cl.
*G01N 33/68* (2006.01)
*C12Q 1/25* (2006.01)

(52) U.S. Cl.
CPC .......... *G01N 33/6896* (2013.01); *C12Q 1/25* (2013.01); *G01N 2333/9015* (2013.01); *G01N 2500/02* (2013.01); *G01N 2800/60* (2013.01)

(58) Field of Classification Search
CPC ................ C12Q 1/25; C12Q 2600/136; G01N 2333/9015; G01N 2500/00; G01N 2500/02; G01N 2800/28; G01N 2800/30; G01N 2800/60; G01N 33/6896
See application file for complete search history.

(56) References Cited

U.S. PATENT DOCUMENTS

| | | |
|---|---|---|
| 2015/0175998 A1 | 6/2015 | Statsyuk et al. |
| 2017/0275341 A1 | 9/2017 | Zhang et al. |
| 2018/0305689 A1 | 10/2018 | Sætrom et al. |

FOREIGN PATENT DOCUMENTS

| | | |
|---|---|---|
| WO | WO 1999/32619 | 7/1999 |
| WO | WO 1999/49029 | 9/1999 |
| WO | WO 1999/53050 | 10/1999 |
| WO | WO 200134815 | 5/2001 |
| WO | WO2014004572 | 1/2014 |
| WO | WO 2017081223 | 5/2017 |

OTHER PUBLICATIONS

Ramirez et al., "Quantitative proteomics reveals neuronal ubiquitination of Rngo/Ddi1 and several proteasomal subunits by Ube3a, accounting for the complexity of Angelman syndrome," Hum. Mol. Genet., 2018, vol. 27, issue 11, pp. 1955-1971.*
Pandya et al., "Secreted retrovirus-like GAG-domain-containing protein PEG10 is regulated by UBE3A and is involved in Angelman syndrome pathophysiology," Cell Rep Med., Aug. 17, 2021; 2(8):100360, pp. 1-26.*
Martínez-Noël, et al., "Identification and Proteomic Analysis of Distinct UBE3A/E6AP Protein Complexes", Molecular and Cellular Biology, 32:3095-3106 (2012).
Kühnle, et al., "Physical and Functional Interaction of the HECT Ubiquitin-protein Ligases E6AP and HERC2", The Journal of Biological Chemistry, 286:19410-19416 (2011).
George, et al,. "A Comprehensive Atlas of E3 Ubiquitin Ligase Mutations in Neurological Disorders", Frontiers in Genetics, 9:1-17 (2018).
Plubell, et al., "Extended Multiplexing of Tandem Mass Tages (TMT) Labeling Reveals Age and High Fat Diet Specificafic Proteome Changes in Mouse Epididymal Adipose Tissue". Molecular & Cellular Proteomics, 16:873-890 (2017).
Ritchie, M.E., et al., Limma powers differential expression analysis for RNA-sequencing an microarray studies. Nucleic Acids Research 43:e47 (2015).
Phipson, et al., "Robust hyperparameter estimation protects against hypervariable genes and improves power to detect differential expression". Annals of Applied Statistics 10:946-963 (2016).
Hothorn, et al., "Simultaneous Interfence in General Parametric Models". Biometrical Journal 50:346-363 (2008).
Lenth, R., "Least Squares Means: The R Package lsmeans". Journal of Statistical Software, 69:1-33 (2016).
Benjamini, et al., "Controlling the false discovery rate: a practical and powerful approach to multiple testing". Journal of the Royal Statistical Society Series B 57:289-300 (1995).
Costa, et al., "MTORC1 Inhibition Corrects Neurodevelopmental and Synaptic Alterations in Human Stem Cell Model of Tuberous Sclerosis", Cell Rep., 15:86-95 (2016).

(Continued)

*Primary Examiner* — Galina M. Yakovleva
(74) *Attorney, Agent, or Firm* — McDonnell Boehnen Hulbert & Berghoff LLP

(57) ABSTRACT

The invention relates to UBE3A protein targets and their usage as target engagement biomarkers for compounds that modulate ube3a expression.

Figure 1A:
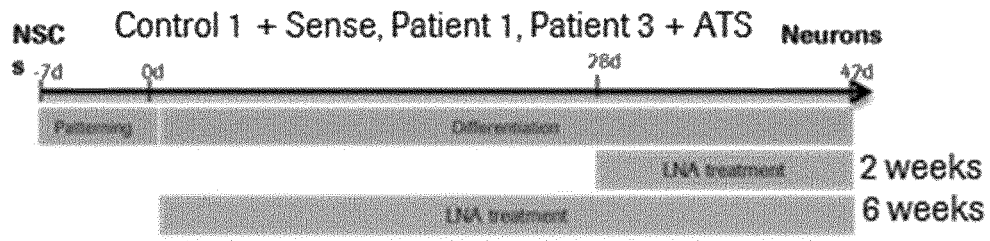

15 Claims, 10 Drawing Sheets
Specification includes a Sequence Listing.

(56) References Cited

OTHER PUBLICATIONS

Dunkley, et al., "Characterization of human pluripotent stem cell derived model of neuronal development sing multiplexed targeted proteomics," Proteomics Clin. App. 9:684-694 (2014).
Huang, et al., "Topoisomerase inhibitors unsilence the dormant allele of Ube3a in neurons". Nature, 481:185-189 (2011).
Nie, et al., "Ankyrin Repeats of ANKRA2 Recongnize a PxLPxL Motif on the 3M Syndrome Protein CCDC8", Stucture, 23:700-712 (2015).
Elbashir, et al., "RNA interference is mediated by 21-and22-nucleotide RNAs", Genes Dev., 15:188-200 (2001).

\* cited by examiner

SEQUENCE LISTING

<160> NUMBER OF SEQ ID NOS: 36

<210> SEQ ID NO 1
<211> LENGTH: 1871
<212> TYPE: PRT
<213> ORGANISM: Homo sapiens

<400> SEQUENCE: 1

Met Glu Asn Glu Ile Phe Thr Pro Leu Leu Glu Gln Phe Met Thr Ser
1               5                   10                  15

Pro Leu Val Thr Trp Val Lys Thr Phe Gly Pro Leu Ala Ala Gly Asn
            20                  25                  30

Gly Thr Asn Leu Asp Glu Tyr Val Ala Leu Val Asp Gly Val Phe Leu
        35                  40                  45

Asn Gln Val Met Leu Gln Ile Asn Pro Lys Leu Glu Ser Gln Arg Val
    50                  55                  60

Asn Lys Lys Val Asn Asn Asp Ala Ser Leu Arg Met His Asn Leu Ser
65                  70                  75                  80

Ile Leu Val Arg Gln Ile Lys Phe Tyr Tyr Gln Glu Thr Leu Gln Gln
                85                  90                  95

Leu Ile Met Met Ser Leu Pro Asn Val Leu Ile Ile Gly Lys Asn Pro
            100                 105                 110

Phe Ser Glu Gln Gly Thr Glu Glu Val Lys Lys Leu Leu Leu Leu Leu
        115                 120                 125

Leu Gly Cys Ala Val Gln Cys Gln Lys Lys Glu Glu Phe Ile Glu Arg
    130                 135                 140

Ile Gln Gly Leu Asp Phe Asp Thr Lys Ala Ala Val Ala Ala His Ile
145                 150                 155                 160

Gln Glu Val Thr His Asn Gln Glu Asn Val Phe Asp Leu Gln Trp Met
                165                 170                 175

Glu Val Thr Asp Met Ser Gln Glu Asp Ile Glu Pro Leu Leu Lys Asn
            180                 185                 190

Met Ala Leu His Leu Lys Arg Leu Ile Asp Glu Arg Asp Glu His Ser
        195                 200                 205

Glu Thr Ile Ile Glu Leu Ser Glu Glu Arg Asp Gly Leu His Phe Leu
    210                 215                 220

```
Pro His Ala Ser Ser Ala Gln Ser Pro Cys Gly Ser Pro Gly Met
225                 230                 235                 240

Lys Arg Thr Glu Ser Arg Gln His Leu Ser Val Glu Leu Ala Asp Ala
                245                 250                 255

Lys Ala Lys Ile Arg Arg Leu Arg Gln Glu Leu Glu Glu Lys Thr Glu
                260                 265                 270

Gln Leu Leu Asp Cys Lys Gln Glu Leu Glu Gln Met Glu Ile Glu Leu
                275                 280                 285

Lys Arg Leu Gln Gln Glu Asn Met Asn Leu Leu Ser Asp Ala Arg Ser
290                 295                 300

Ala Arg Met Tyr Arg Asp Glu Leu Asp Ala Leu Arg Glu Lys Ala Val
305                 310                 315                 320

Arg Val Asp Lys Leu Glu Ser Glu Val Ser Arg Tyr Lys Glu Arg Leu
                325                 330                 335

His Asp Ile Glu Phe Tyr Lys Ala Arg Val Glu Glu Leu Lys Glu Asp
                340                 345                 350

Asn Gln Val Leu Leu Glu Thr Lys Thr Met Leu Glu Asp Gln Leu Glu
                355                 360                 365

Gly Thr Arg Ala Arg Ser Asp Lys Leu His Glu Leu Glu Lys Glu Asn
370                 375                 380

Leu Gln Leu Lys Ala Lys Leu His Asp Met Glu Met Glu Arg Asp Met
385                 390                 395                 400

Asp Arg Lys Lys Ile Glu Glu Leu Met Glu Asn Met Thr Leu Glu
                405                 410                 415

Met Ala Gln Lys Gln Ser Met Asp Glu Ser Leu His Leu Gly Trp Glu
                420                 425                 430

Leu Glu Gln Ile Ser Arg Thr Ser Glu Leu Ser Glu Ala Pro Gln Lys
                435                 440                 445

Ser Leu Gly His Glu Val Asn Glu Leu Thr Ser Ser Arg Leu Leu Lys
                450                 455                 460

Leu Glu Met Glu Asn Gln Ser Leu Thr Lys Thr Val Glu Glu Leu Arg
465                 470                 475                 480

Thr Thr Val Asp Ser Val Glu Gly Asn Ala Ser Lys Ile Leu Lys Met
                485                 490                 495

Glu Lys Glu Asn Gln Arg Leu Ser Lys Lys Val Glu Ile Leu Glu Asn
                500                 505                 510

Glu Ile Val Gln Glu Lys Gln Ser Leu Gln Asn Cys Gln Asn Leu Ser
                515                 520                 525

Lys Asp Leu Met Lys Glu Lys Ala Gln Leu Glu Lys Thr Ile Glu Thr
530                 535                 540

Leu Arg Glu Asn Ser Glu Arg Gln Ile Lys Ile Leu Glu Gln Glu Asn
545                 550                 555                 560

Glu His Leu Asn Gln Thr Val Ser Ser Leu Arg Gln Arg Ser Gln Ile
                565                 570                 575

Ser Ala Glu Ala Arg Val Lys Asp Ile Glu Lys Glu Asn Lys Ile Leu
                580                 585                 590

His Glu Ser Ile Lys Glu Thr Ser Ser Lys Leu Ser Lys Ile Glu Phe
                595                 600                 605

Glu Lys Arg Gln Ile Lys Lys Glu Leu Glu His Tyr Lys Glu Lys Gly
                610                 615                 620

Glu Arg Ala Glu Glu Leu Glu Asn Glu Leu His His Leu Glu Lys Glu
625                 630                 635                 640

Asn Glu Leu Leu Gln Lys Lys Ile Thr Asn Leu Lys Ile Thr Cys Glu
```

```
                    645                 650                 655
Lys Ile Glu Ala Leu Glu Gln Glu Asn Ser Glu Leu Glu Arg Glu Asn
                660                 665                 670

Arg Lys Leu Lys Lys Thr Leu Asp Ser Phe Lys Asn Leu Thr Phe Gln
            675                 680                 685

Leu Glu Ser Leu Glu Lys Glu Asn Ser Gln Leu Asp Glu Glu Asn Leu
        690                 695                 700

Glu Leu Arg Arg Asn Val Glu Ser Leu Lys Cys Ala Ser Met Lys Met
705                 710                 715                 720

Ala Gln Leu Gln Leu Glu Asn Lys Glu Leu Glu Ser Glu Lys Glu Gln
                725                 730                 735

Leu Lys Lys Gly Leu Glu Leu Leu Lys Ala Ser Phe Lys Lys Thr Glu
            740                 745                 750

Arg Leu Glu Val Ser Tyr Gln Gly Leu Asp Ile Glu Asn Gln Arg Leu
        755                 760                 765

Gln Lys Thr Leu Glu Asn Ser Asn Lys Lys Ile Gln Gln Leu Glu Ser
    770                 775                 780

Glu Leu Gln Asp Leu Glu Met Glu Asn Gln Thr Leu Gln Lys Asn Leu
785                 790                 795                 800

Glu Glu Leu Lys Ile Ser Ser Lys Arg Leu Glu Gln Leu Glu Lys Glu
                805                 810                 815

Asn Lys Ser Leu Glu Gln Glu Thr Ser Gln Leu Glu Lys Asp Lys Lys
            820                 825                 830

Gln Leu Glu Lys Glu Asn Lys Arg Leu Arg Gln Gln Ala Glu Ile Lys
        835                 840                 845

Asp Thr Thr Leu Glu Glu Asn Asn Val Lys Ile Gly Asn Leu Glu Lys
    850                 855                 860

Glu Asn Lys Thr Leu Ser Lys Glu Ile Gly Ile Tyr Lys Glu Ser Cys
865                 870                 875                 880

Val Arg Leu Lys Glu Leu Glu Lys Glu Asn Lys Glu Leu Val Lys Arg
                885                 890                 895

Ala Thr Ile Asp Ile Lys Thr Leu Val Thr Leu Arg Glu Asp Leu Val
            900                 905                 910

Ser Glu Lys Leu Lys Thr Gln Gln Met Asn Asn Asp Leu Glu Lys Leu
        915                 920                 925

Thr His Glu Leu Glu Lys Ile Gly Leu Asn Lys Glu Arg Leu Leu His
    930                 935                 940

Asp Glu Gln Ser Thr Asp Asp Ser Arg Tyr Lys Leu Leu Glu Ser Lys
945                 950                 955                 960

Leu Glu Ser Thr Leu Lys Lys Ser Leu Glu Ile Lys Glu Glu Lys Ile
                965                 970                 975

Ala Ala Leu Glu Ala Arg Leu Glu Glu Ser Thr Asn Tyr Asn Gln Gln
            980                 985                 990

Leu Arg Gln Glu Leu Lys Thr Val Lys Lys Asn Tyr Glu Ala Leu Lys
        995                 1000                1005

Gln Arg Gln Asp Glu Glu Arg Met Val Gln Ser Ser Pro Pro Ile
        1010                1015                1020

Ser Gly Glu Asp Asn Lys Trp Glu Arg Glu Ser Gln Glu Thr Thr
        1025                1030                1035

Arg Glu Leu Leu Lys Val Lys Asp Arg Leu Ile Glu Val Glu Arg
        1040                1045                1050

Asn Asn Ala Thr Leu Gln Ala Glu Lys Gln Ala Leu Lys Thr Gln
        1055                1060                1065
```

```
Leu Lys Gln Leu Glu Thr Gln Asn Asn Leu Gln Ala Gln Ile
    1070                1075                1080

Leu Ala Leu Gln Arg Gln Thr Val Ser Leu Gln Glu Gln Asn Thr
    1085                1090                1095

Thr Leu Gln Thr Gln Asn Ala Lys Leu Gln Val Glu Asn Ser Thr
    1100                1105                1110

Leu Asn Ser Gln Ser Thr Ser Leu Met Asn Gln Asn Ala Gln Leu
    1115                1120                1125

Leu Ile Gln Gln Ser Ser Leu Glu Asn Glu Asn Glu Ser Val Ile
    1130                1135                1140

Lys Glu Arg Glu Asp Leu Lys Ser Leu Tyr Asp Ser Leu Ile Lys
    1145                1150                1155

Asp His Glu Lys Leu Glu Leu Leu His Glu Arg Gln Ala Ser Glu
    1160                1165                1170

Tyr Glu Ser Leu Ile Ser Lys His Gly Thr Leu Lys Ser Ala His
    1175                1180                1185

Lys Asn Leu Glu Val Glu His Arg Asp Leu Glu Asp Arg Tyr Asn
    1190                1195                1200

Gln Leu Leu Lys Gln Lys Gly Gln Leu Glu Asp Leu Glu Lys Met
    1205                1210                1215

Leu Lys Val Glu Gln Glu Lys Met Leu Leu Glu Asn Lys Asn His
    1220                1225                1230

Glu Thr Val Ala Ala Glu Tyr Lys Lys Leu Cys Gly Glu Asn Asp
    1235                1240                1245

Arg Leu Asn His Thr Tyr Ser Gln Leu Leu Lys Glu Thr Glu Val
    1250                1255                1260

Leu Gln Thr Asp His Lys Asn Leu Lys Ser Leu Leu Asn Asn Ser
    1265                1270                1275

Lys Leu Glu Gln Thr Arg Leu Glu Ala Glu Phe Ser Lys Leu Lys
    1280                1285                1290

Glu Gln Tyr Gln Gln Leu Asp Ile Thr Ser Thr Lys Leu Asn Asn
    1295                1300                1305

Gln Cys Glu Leu Leu Ser Gln Leu Lys Gly Asn Leu Glu Glu Glu
    1310                1315                1320

Asn Arg His Leu Leu Asp Gln Ile Gln Thr Leu Met Leu Gln Asn
    1325                1330                1335

Arg Thr Leu Leu Glu Gln Asn Met Glu Ser Lys Asp Leu Phe His
    1340                1345                1350

Val Glu Gln Arg Gln Tyr Ile Asp Lys Leu Asn Glu Leu Arg Arg
    1355                1360                1365

Gln Lys Glu Lys Leu Glu Glu Lys Ile Met Asp Gln Tyr Lys Phe
    1370                1375                1380

Tyr Asp Pro Ser Pro Pro Arg Arg Arg Gly Asn Trp Ile Thr Leu
    1385                1390                1395

Lys Met Arg Lys Leu Ile Lys Ser Lys Lys Asp Ile Asn Arg Glu
    1400                1405                1410

Arg Gln Lys Ser Leu Thr Leu Thr Pro Thr Arg Ser Asp Ser Ser
    1415                1420                1425

Glu Gly Phe Leu Gln Leu Pro His Gln Asp Ser Gln Asp Ser Ser
    1430                1435                1440

Ser Val Gly Ser Asn Ser Leu Glu Asp Gly Gln Thr Leu Gly Thr
    1445                1450                1455
```

```
Lys Lys Ser Ser Met Val Ala Leu Lys Arg Leu Pro Phe Leu Arg
    1460            1465            1470

Asn Arg Pro Lys Asp Lys Asp Lys Met Lys Ala Cys Tyr Arg Arg
    1475            1480            1485

Ser Met Ser Met Asn Asp Leu Val Gln Ser Met Val Leu Ala Gly
    1490            1495            1500

Gln Trp Thr Gly Ser Thr Glu Asn Leu Glu Val Pro Asp Asp Ile
    1505            1510            1515

Ser Thr Gly Lys Arg Arg Lys Glu Leu Gly Ala Met Ala Phe Ser
    1520            1525            1530

Thr Thr Ala Ile Asn Phe Ser Thr Val Asn Ser Ser Ala Gly Phe
    1535            1540            1545

Arg Ser Lys Gln Leu Val Asn Asn Lys Asp Thr Thr Ser Phe Glu
    1550            1555            1560

Asp Ile Ser Pro Gln Gly Val Ser Asp Asp Ser Ser Thr Gly Ser
    1565            1570            1575

Arg Val His Ala Ser Arg Pro Ala Ser Leu Asp Ser Gly Arg Thr
    1580            1585            1590

Ser Thr Ser Asn Ser Asn Asn Asn Ala Ser Leu His Glu Val Lys
    1595            1600            1605

Ala Gly Ala Val Asn Asn Gln Ser Arg Pro Gln Ser His Ser Ser
    1610            1615            1620

Gly Glu Phe Ser Leu Leu His Asp His Glu Ala Trp Ser Ser Ser
    1625            1630            1635

Gly Ser Ser Pro Ile Gln Tyr Leu Lys Arg Gln Thr Arg Ser Ser
    1640            1645            1650

Pro Val Leu Gln His Lys Ile Ser Glu Thr Leu Glu Ser Arg His
    1655            1660            1665

His Lys Ile Lys Thr Gly Ser Pro Gly Ser Glu Val Val Thr Leu
    1670            1675            1680

Gln Gln Phe Leu Glu Glu Ser Asn Lys Leu Thr Ser Val Gln Ile
    1685            1690            1695

Lys Ser Ser Ser Gln Glu Asn Leu Leu Asp Glu Val Met Lys Ser
    1700            1705            1710

Leu Ser Val Ser Ser Asp Phe Leu Gly Lys Asp Lys Pro Val Ser
    1715            1720            1725

Cys Gly Leu Ala Arg Ser Val Ser Gly Lys Thr Pro Gly Asp Phe
    1730            1735            1740

Tyr Asp Arg Arg Thr Thr Lys Pro Glu Phe Leu Arg Pro Gly Pro
    1745            1750            1755

Arg Lys Thr Glu Asp Thr Tyr Phe Ile Ser Ser Ala Gly Lys Pro
    1760            1765            1770

Thr Pro Gly Thr Gln Gly Lys Ile Lys Leu Val Lys Glu Ser Ser
    1775            1780            1785

Leu Ser Arg Gln Ser Lys Asp Ser Asn Pro Tyr Ala Thr Leu Pro
    1790            1795            1800

Arg Ala Ser Ser Val Ile Ser Thr Ala Glu Gly Thr Thr Arg Arg
    1805            1810            1815

Thr Ser Ile His Asp Phe Leu Thr Lys Asp Ser Arg Leu Pro Ile
    1820            1825            1830

Ser Val Asp Ser Pro Pro Ala Ala Ala Asp Ser Asn Thr Thr Ala
    1835            1840            1845

Ala Ser Asn Val Asp Lys Val Gln Glu Ser Arg Asn Ser Lys Ser
```

```
            1850                1855            1860
Arg Ser  Arg Glu Gln Gln Ser  Ser
    1865              1870

<210> SEQ ID NO 2
<211> LENGTH: 7570
<212> TYPE: PRT
<213> ORGANISM: Homo sapiens

<400> SEQUENCE: 2

Met Ala Gly Tyr Leu Ser Pro Ala Ala Tyr Leu Tyr Val Glu Glu Gln
1               5                   10                  15

Glu Tyr Leu Gln Ala Tyr Glu Asp Val Leu Glu Arg Tyr Lys Asp Glu
            20                  25                  30

Arg Asp Lys Val Gln Lys Lys Thr Phe Thr Lys Trp Ile Asn Gln His
        35                  40                  45

Leu Met Lys Val Arg Lys His Val Asn Asp Leu Tyr Glu Asp Leu Arg
    50                  55                  60

Asp Gly His Asn Leu Ile Ser Leu Leu Glu Val Leu Ser Gly Asp Thr
65                  70                  75                  80

Leu Pro Arg Glu Lys Gly Arg Met Arg Phe His Arg Leu Gln Asn Val
                85                  90                  95

Gln Ile Ala Leu Asp Tyr Leu Lys Arg Arg Gln Val Lys Leu Val Asn
            100                 105                 110

Ile Arg Asn Asp Asp Ile Thr Asp Gly Asn Pro Lys Leu Thr Leu Gly
        115                 120                 125

Leu Ile Trp Thr Ile Ile Leu His Phe Gln Ile Ser Asp Ile His Val
    130                 135                 140

Thr Gly Glu Ser Glu Asp Met Ser Ala Lys Glu Arg Leu Leu Leu Trp
145                 150                 155                 160

Thr Gln Gln Ala Thr Glu Gly Tyr Ala Gly Ile Arg Cys Glu Asn Phe
                165                 170                 175

Thr Thr Cys Trp Arg Asp Gly Lys Leu Phe Asn Ala Ile Ile His Lys
            180                 185                 190

Tyr Arg Pro Asp Leu Ile Asp Met Asn Thr Val Ala Val Gln Ser Asn
        195                 200                 205

Leu Ala Asn Leu Glu His Ala Phe Tyr Val Ala Glu Lys Ile Gly Val
    210                 215                 220

Ile Arg Leu Leu Asp Pro Glu Asp Val Asp Val Ser Ser Pro Asp Glu
225                 230                 235                 240

Lys Ser Val Ile Thr Tyr Val Ser Ser Leu Tyr Asp Ala Phe Pro Lys
                245                 250                 255

Val Pro Glu Gly Gly Glu Gly Ile Gly Ala Asn Asp Val Glu Val Lys
            260                 265                 270

Trp Ile Glu Tyr Gln Asn Met Val Asn Tyr Leu Ile Gln Trp Ile Arg
        275                 280                 285

His His Val Thr Thr Met Ser Glu Arg Thr Phe Pro Asn Asn Pro Val
    290                 295                 300

Glu Leu Lys Ala Leu Tyr Asn Gln Tyr Leu Gln Phe Lys Glu Thr Glu
305                 310                 315                 320

Ile Pro Pro Lys Glu Thr Glu Lys Ser Lys Ile Lys Arg Leu Tyr Lys
                325                 330                 335

Leu Leu Glu Ile Trp Ile Glu Phe Gly Arg Ile Lys Leu Leu Gln Gly
            340                 345                 350
```

```
Tyr His Pro Asn Asp Ile Glu Lys Glu Trp Gly Lys Leu Ile Ile Ala
        355                 360                 365
Met Leu Glu Arg Glu Lys Ala Leu Arg Pro Val Glu Arg Leu Glu
    370                 375                 380
Met Leu Gln Gln Ile Ala Asn Arg Val Gln Arg Asp Ser Val Ile Cys
385                 390                 395                 400
Glu Asp Lys Leu Ile Leu Ala Gly Asn Ala Leu Gln Ser Asp Ser Lys
                405                 410                 415
Arg Leu Glu Ser Gly Val Gln Phe Gln Asn Glu Ala Glu Ile Ala Gly
            420                 425                 430
Tyr Ile Leu Glu Cys Glu Asn Leu Leu Arg Gln His Val Ile Asp Val
        435                 440                 445
Gln Ile Leu Ile Asp Gly Lys Tyr Tyr Gln Ala Asp Gln Leu Val Gln
    450                 455                 460
Arg Val Ala Lys Leu Arg Asp Glu Ile Met Ala Leu Arg Asn Glu Cys
465                 470                 475                 480
Ser Ser Val Tyr Ser Lys Gly Arg Ile Leu Thr Thr Glu Gln Thr Lys
                485                 490                 495
Leu Met Ile Ser Gly Ile Thr Gln Ser Leu Asn Ser Gly Phe Ala Gln
            500                 505                 510
Thr Leu His Pro Ser Leu Thr Ser Gly Leu Thr Gln Ser Leu Thr Pro
        515                 520                 525
Ser Leu Thr Ser Ser Met Thr Ser Gly Leu Ser Ser Gly Met Thr
    530                 535                 540
Ser Arg Leu Thr Pro Ser Val Thr Pro Ala Tyr Thr Pro Gly Phe Pro
545                 550                 555                 560
Ser Gly Leu Val Pro Asn Phe Ser Ser Gly Val Glu Pro Asn Ser Leu
                565                 570                 575
Gln Thr Leu Lys Leu Met Gln Ile Arg Lys Pro Leu Leu Lys Ser Ser
            580                 585                 590
Leu Leu Asp Gln Asn Leu Thr Glu Glu Ile Asn Met Lys Phe Val
    595                 600                 605
Gln Asp Leu Leu Asn Trp Val Asp Glu Met Gln Val Gln Leu Asp Arg
610                 615                 620
Thr Glu Trp Gly Ser Asp Leu Pro Ser Val Glu Ser His Leu Glu Asn
625                 630                 635                 640
His Lys Asn Val His Arg Ala Ile Glu Glu Phe Glu Ser Ser Leu Lys
                645                 650                 655
Glu Ala Lys Ile Ser Glu Ile Gln Met Thr Ala Pro Leu Lys Leu Thr
            660                 665                 670
Tyr Ala Glu Lys Leu His Arg Leu Glu Ser Gln Tyr Ala Lys Leu Leu
        675                 680                 685
Asn Thr Ser Arg Asn Gln Glu Arg His Leu Asp Thr Leu His Asn Phe
    690                 695                 700
Val Ser Arg Ala Thr Asn Glu Leu Ile Trp Leu Asn Glu Lys Glu Glu
705                 710                 715                 720
Glu Glu Val Ala Tyr Asp Trp Ser Arg Asn Thr Asn Ile Ala Arg
                725                 730                 735
Lys Lys Asp Tyr His Ala Glu Leu Met Arg Glu Leu Asp Gln Lys Glu
            740                 745                 750
Glu Asn Ile Lys Ser Val Gln Glu Ile Ala Glu Gln Leu Leu Leu Glu
        755                 760                 765
Asn His Pro Ala Arg Leu Thr Ile Glu Ala Tyr Arg Ala Ala Met Gln
```

```
                770             775             780
Thr Gln Trp Ser Trp Ile Leu Gln Leu Cys Gln Cys Val Glu Gln His
785             790             795             800

Ile Lys Glu Asn Thr Ala Tyr Phe Glu Phe Phe Asn Asp Ala Lys Glu
            805             810             815

Ala Thr Asp Tyr Leu Arg Asn Leu Lys Asp Ala Ile Gln Arg Lys Tyr
            820             825             830

Ser Cys Asp Arg Ser Ser Ile His Lys Leu Glu Asp Leu Val Gln
            835             840             845

Glu Ser Met Glu Glu Lys Glu Glu Leu Leu Gln Tyr Lys Ser Thr Ile
850             855             860

Ala Asn Leu Met Gly Lys Ala Lys Thr Ile Ile Gln Leu Lys Pro Arg
865             870             875             880

Asn Ser Asp Cys Pro Leu Lys Thr Ser Ile Pro Ile Lys Ala Ile Cys
            885             890             895

Asp Tyr Arg Gln Ile Glu Ile Thr Ile Tyr Lys Asp Asp Glu Cys Val
            900             905             910

Leu Ala Asn Asn Ser His Arg Ala Lys Trp Lys Val Ile Ser Pro Thr
            915             920             925

Gly Asn Glu Ala Met Val Pro Ser Val Cys Phe Thr Val Pro Pro Pro
930             935             940

Asn Lys Glu Ala Val Asp Leu Ala Asn Arg Ile Glu Gln Gln Tyr Gln
945             950             955             960

Asn Val Leu Thr Leu Trp His Glu Ser His Ile Asn Met Lys Ser Val
            965             970             975

Val Ser Trp His Tyr Leu Ile Asn Glu Ile Asp Arg Ile Arg Ala Ser
            980             985             990

Asn Val Ala Ser Ile Lys Thr Met Leu Pro Gly Glu His Gln Gln Val
            995             1000            1005

Leu Ser Asn Leu Gln Ser Arg Phe Glu Asp Phe Leu Glu Asp Ser
    1010            1015            1020

Gln Glu Ser Gln Val Phe Ser Gly Ser Asp Ile Thr Gln Leu Glu
    1025            1030            1035

Lys Glu Val Asn Val Cys Lys Gln Tyr Tyr Gln Glu Leu Leu Lys
    1040            1045            1050

Ser Ala Glu Arg Glu Gln Glu Glu Ser Val Tyr Asn Leu Tyr
    1055            1060            1065

Ile Ser Glu Val Arg Asn Ile Arg Leu Arg Leu Glu Asn Cys Glu
    1070            1075            1080

Asp Arg Leu Ile Arg Gln Ile Arg Thr Pro Leu Glu Arg Asp Asp
    1085            1090            1095

Leu His Glu Ser Val Phe Arg Ile Thr Glu Gln Glu Lys Leu Lys
    1100            1105            1110

Lys Glu Leu Glu Arg Leu Lys Asp Asp Leu Gly Thr Ile Thr Asn
    1115            1120            1125

Lys Cys Glu Glu Phe Phe Ser Gln Ala Ala Ala Ser Ser Ser Val
    1130            1135            1140

Pro Thr Leu Arg Ser Glu Leu Asn Val Leu Gln Asn Met Asn
    1145            1150            1155

Gln Val Tyr Ser Met Ser Ser Thr Tyr Ile Asp Lys Leu Lys Thr
    1160            1165            1170

Val Asn Leu Val Leu Lys Asn Thr Gln Ala Ala Glu Ala Leu Val
    1175            1180            1185
```

```
Lys Leu Tyr Glu Thr Lys Leu Cys Glu Glu Ala Val Ile Ala
1190             1195             1200

Asp Lys Asn Asn Ile Glu Asn Leu Ile Ser Thr Leu Lys Gln Trp
1205             1210             1215

Arg Ser Glu Val Asp Glu Lys Arg Gln Val Phe His Ala Leu Glu
1220             1225             1230

Asp Glu Leu Gln Lys Ala Lys Ala Ile Ser Asp Glu Met Phe Lys
1235             1240             1245

Thr Tyr Lys Glu Arg Asp Leu Asp Phe Asp Trp His Lys Glu Lys
1250             1255             1260

Ala Asp Gln Leu Val Glu Arg Trp Gln Asn Val His Val Gln Ile
1265             1270             1275

Asp Asn Arg Leu Arg Asp Leu Glu Gly Ile Gly Lys Ser Leu Lys
1280             1285             1290

Tyr Tyr Arg Asp Thr Tyr His Pro Leu Asp Asp Trp Ile Gln Gln
1295             1300             1305

Val Glu Thr Thr Gln Arg Lys Ile Gln Glu Asn Gln Pro Glu Asn
1310             1315             1320

Ser Lys Thr Leu Ala Thr Gln Leu Asn Gln Gln Lys Met Leu Val
1325             1330             1335

Ser Glu Ile Glu Met Lys Gln Ser Lys Met Asp Glu Cys Gln Lys
1340             1345             1350

Tyr Ala Glu Gln Tyr Ser Ala Thr Val Lys Asp Tyr Glu Leu Gln
1355             1360             1365

Thr Met Thr Tyr Arg Ala Met Val Asp Ser Gln Gln Lys Ser Pro
1370             1375             1380

Val Lys Arg Arg Arg Met Gln Ser Ser Ala Asp Leu Ile Ile Gln
1385             1390             1395

Glu Phe Met Asp Leu Arg Thr Arg Tyr Thr Ala Leu Val Thr Leu
1400             1405             1410

Met Thr Gln Tyr Ile Lys Phe Ala Gly Asp Ser Leu Lys Arg Leu
1415             1420             1425

Glu Glu Glu Glu Lys Ser Leu Glu Glu Glu Lys Lys Glu His Val
1430             1435             1440

Glu Lys Ala Lys Glu Leu Gln Lys Trp Val Ser Asn Ile Ser Lys
1445             1450             1455

Thr Leu Lys Asp Ala Glu Lys Ala Gly Lys Pro Pro Phe Ser Lys
1460             1465             1470

Gln Lys Ile Ser Ser Glu Glu Ile Ser Thr Lys Lys Glu Gln Leu
1475             1480             1485

Ser Glu Ala Leu Gln Thr Ile Gln Leu Phe Leu Ala Lys His Gly
1490             1495             1500

Asp Lys Met Thr Asp Glu Glu Arg Asn Glu Leu Glu Lys Gln Val
1505             1510             1515

Lys Thr Leu Gln Glu Ser Tyr Asn Leu Leu Phe Ser Glu Ser Leu
1520             1525             1530

Lys Gln Leu Gln Glu Ser Gln Thr Ser Gly Asp Val Lys Val Glu
1535             1540             1545

Glu Lys Leu Asp Lys Val Ile Ala Gly Thr Ile Asp Gln Thr Thr
1550             1555             1560

Gly Glu Val Leu Ser Val Phe Gln Ala Val Leu Arg Gly Leu Ile
1565             1570             1575
```

```
Asp Tyr Asp Thr Gly Ile Arg Leu Leu Glu Thr Gln Leu Met Ile
    1580            1585                1590

Ser Gly Leu Ile Ser Pro Glu Leu Arg Lys Cys Phe Asp Leu Lys
    1595            1600                1605

Asp Ala Lys Ser His Gly Leu Ile Asp Glu Gln Ile Leu Cys Gln
    1610            1615                1620

Leu Lys Glu Leu Ser Lys Ala Lys Glu Ile Ile Ser Ala Ala Ser
    1625            1630                1635

Pro Thr Thr Ile Pro Val Leu Asp Ala Leu Ala Gln Ser Met Ile
    1640            1645                1650

Thr Glu Ser Met Ala Ile Lys Val Leu Glu Ile Leu Leu Ser Thr
    1655            1660                1665

Gly Ser Leu Val Ile Pro Ala Thr Gly Glu Gln Leu Thr Leu Gln
    1670            1675                1680

Lys Ala Phe Gln Gln Asn Leu Val Ser Ser Ala Leu Phe Ser Lys
    1685            1690                1695

Val Leu Glu Arg Gln Asn Met Cys Lys Asp Leu Ile Asp Pro Cys
    1700            1705                1710

Thr Ser Glu Lys Val Ser Leu Ile Asp Met Val Gln Arg Ser Thr
    1715            1720                1725

Leu Gln Glu Asn Thr Gly Met Trp Leu Leu Pro Val Arg Pro Gln
    1730            1735                1740

Glu Gly Gly Arg Ile Thr Leu Lys Cys Gly Arg Asn Ile Ser Ile
    1745            1750                1755

Leu Arg Ala Ala His Glu Gly Leu Ile Asp Arg Glu Thr Met Phe
    1760            1765                1770

Arg Leu Leu Ser Ala Gln Leu Leu Ser Gly Gly Leu Ile Asn Ser
    1775            1780                1785

Asn Ser Gly Gln Arg Met Thr Val Glu Glu Ala Val Arg Glu Gly
    1790            1795                1800

Val Ile Asp Arg Asp Thr Ala Ser Ser Ile Leu Thr Tyr Gln Val
    1805            1810                1815

Gln Thr Gly Gly Ile Ile Gln Ser Asn Pro Ala Lys Arg Leu Thr
    1820            1825                1830

Val Asp Glu Ala Val Gln Cys Asp Leu Ile Thr Ser Ser Ser Ala
    1835            1840                1845

Leu Leu Val Leu Glu Ala Gln Arg Gly Tyr Val Gly Leu Ile Trp
    1850            1855                1860

Pro His Ser Gly Glu Ile Phe Pro Thr Ser Ser Ser Leu Gln Gln
    1865            1870                1875

Glu Leu Ile Thr Asn Glu Leu Ala Tyr Lys Ile Leu Asn Gly Arg
    1880            1885                1890

Gln Lys Ile Ala Ala Leu Tyr Ile Pro Glu Ser Ser Gln Val Ile
    1895            1900                1905

Gly Leu Asp Ala Ala Lys Gln Leu Gly Ile Ile Asp Asn Asn Thr
    1910            1915                1920

Ala Ser Ile Leu Lys Asn Ile Thr Leu Pro Asp Lys Met Pro Asp
    1925            1930                1935

Leu Gly Asp Leu Glu Ala Cys Lys Asn Ala Arg Arg Trp Leu Ser
    1940            1945                1950

Phe Cys Lys Phe Gln Pro Ser Thr Val His Asp Tyr Arg Gln Glu
    1955            1960                1965

Glu Asp Val Phe Asp Gly Glu Glu Pro Val Thr Thr Gln Thr Ser
```

-continued

```
            1970                1975                1980
Glu Glu Thr Lys Lys Leu Phe Leu Ser Tyr Leu Met Ile Asn Ser
    1985                1990                1995
Tyr Met Asp Ala Asn Thr Gly Gln Arg Leu Leu Leu Tyr Asp Gly
    2000                2005                2010
Asp Leu Asp Glu Ala Val Gly Met Leu Leu Glu Gly Cys His Ala
    2015                2020                2025
Glu Phe Asp Gly Asn Thr Ala Ile Lys Glu Cys Leu Asp Val Leu
    2030                2035                2040
Ser Ser Ser Gly Val Phe Leu Asn Asn Ala Ser Gly Arg Glu Lys
    2045                2050                2055
Asp Glu Cys Thr Ala Thr Pro Ser Ser Phe Asn Lys Cys His Cys
    2060                2065                2070
Gly Glu Pro Glu His Glu Thr Pro Glu Asn Arg Lys Cys Ala
    2075                2080                2085
Ile Asp Glu Glu Phe Asn Glu Met Arg Asn Thr Val Ile Asn Ser
    2090                2095                2100
Glu Phe Ser Gln Ser Gly Lys Leu Ala Ser Thr Ile Ser Ile Asp
    2105                2110                2115
Pro Lys Val Asn Ser Ser Pro Ser Val Cys Val Pro Ser Leu Ile
    2120                2125                2130
Ser Tyr Leu Thr Gln Thr Glu Leu Ala Asp Ile Ser Met Leu Arg
    2135                2140                2145
Ser Asp Ser Glu Asn Ile Leu Thr Asn Tyr Glu Asn Gln Ser Arg
    2150                2155                2160
Val Glu Thr Asn Glu Arg Ala Asn Glu Cys Ser His Ser Lys Asn
    2165                2170                2175
Ile Gln Asn Phe Pro Ser Asp Leu Ile Glu Asn Pro Ile Met Lys
    2180                2185                2190
Ser Lys Met Ser Lys Phe Cys Gly Val Asn Glu Thr Glu Asn Glu
    2195                2200                2205
Asp Asn Thr Asn Arg Asp Ser Pro Ile Phe Asp Tyr Ser Pro Arg
    2210                2215                2220
Leu Ser Ala Leu Leu Ser His Asp Lys Leu Met His Ser Gln Gly
    2225                2230                2235
Ser Phe Asn Asp Thr His Thr Pro Glu Ser Asn Gly Asn Lys Cys
    2240                2245                2250
Glu Ala Pro Ala Leu Ser Phe Ser Asp Lys Thr Met Leu Ser Gly
    2255                2260                2265
Gln Arg Ile Gly Glu Lys Phe Gln Asp Gln Phe Leu Gly Ile Ala
    2270                2275                2280
Ala Ile Asn Ile Ser Leu Pro Gly Glu Gln Tyr Gly Gln Lys Ser
    2285                2290                2295
Leu Asn Met Ile Ser Ser Asn Pro Gln Val Gln Tyr His Asn Asp
    2300                2305                2310
Lys Tyr Ile Ser Asn Thr Ser Gly Glu Asp Glu Lys Thr His Pro
    2315                2320                2325
Gly Phe Gln Gln Met Pro Glu Asp Lys Glu Asp Glu Ser Glu Ile
    2330                2335                2340
Glu Glu Tyr Ser Cys Ala Val Thr Pro Gly Gly Asp Thr Asp Asn
    2345                2350                2355
Ala Ile Val Ser Leu Thr Cys Ala Thr Pro Leu Leu Asp Glu Thr
    2360                2365                2370
```

-continued

```
Ile Ser Ala Ser Asp Tyr Glu Thr Ser Leu Leu Asn Asp Gln Gln
2375                2380                2385

Asn Asn Thr Gly Thr Asp Thr Asp Ser Asp Asp Asp Phe Tyr Asp
2390                2395                2400

Thr Pro Leu Phe Glu Asp Asp Asp His Asp Ser Leu Leu Leu Asp
2405                2410                2415

Gly Asp Asp Arg Asp Cys Leu His Pro Glu Asp Tyr Asp Thr Leu
2420                2425                2430

Gln Glu Glu Asn Asp Glu Thr Ala Ser Pro Ala Asp Val Phe Tyr
2435                2440                2445

Asp Val Ser Lys Glu Asn Asn Ser Met Val Pro Gln Gly Ala
2450                2455                2460

Pro Val Gly Ser Leu Ser Val Lys Asn Lys Ala His Cys Leu Gln
2465                2470                2475

Asp Phe Leu Met Asp Val Glu Lys Asp Glu Leu Asp Ser Gly Glu
2480                2485                2490

Lys Ile His Leu Asn Pro Val Gly Ser Asp Lys Val Asn Gly Gln
2495                2500                2505

Ser Leu Glu Thr Gly Ser Glu Arg Glu Cys Thr Asn Ile Leu Glu
2510                2515                2520

Gly Asp Glu Ser Asp Ser Leu Thr Asp Tyr Asp Ile Val Gly Gly
2525                2530                2535

Lys Glu Ser Phe Thr Ala Ser Leu Lys Phe Asp Asp Ser Gly Ser
2540                2545                2550

Trp Arg Gly Arg Lys Glu Glu Tyr Val Thr Gly Gln Glu Phe His
2555                2560                2565

Ser Asp Thr Asp His Leu Asp Ser Met Gln Ser Glu Glu Ser Tyr
2570                2575                2580

Gly Asp Tyr Ile Tyr Asp Ser Asn Asp Gln Asp Asp Asp Asp Asp
2585                2590                2595

Asp Gly Ile Asp Glu Glu Gly Gly Gly Ile Arg Asp Glu Asn Gly
2600                2605                2610

Lys Pro Arg Cys Gln Asn Val Ala Glu Asp Met Asp Ile Gln Leu
2615                2620                2625

Cys Ala Ser Ile Leu Asn Glu Asn Ser Asp Glu Asn Glu Asn Ile
2630                2635                2640

Asn Thr Met Ile Leu Leu Asp Lys Met His Ser Cys Ser Ser Leu
2645                2650                2655

Glu Lys Gln Gln Arg Val Asn Val Val Gln Leu Ala Ser Pro Ser
2660                2665                2670

Glu Asn Asn Leu Val Thr Glu Lys Ser Asn Leu Pro Glu Tyr Thr
2675                2680                2685

Thr Glu Ile Ala Gly Lys Ser Lys Glu Asn Leu Leu Asn His Glu
2690                2695                2700

Met Val Leu Lys Asp Val Leu Pro Pro Ile Ile Lys Asp Thr Glu
2705                2710                2715

Ser Glu Lys Thr Phe Gly Pro Ala Ser Ile Ser His Asp Asn Asn
2720                2725                2730

Asn Ile Ser Ser Thr Ser Glu Leu Gly Thr Asp Leu Ala Asn Thr
2735                2740                2745

Lys Val Lys Leu Ile Gln Gly Ser Glu Leu Pro Glu Leu Thr Asp
2750                2755                2760
```

```
Ser Val Lys Gly Lys Asp Glu Tyr Phe Lys Asn Met Thr Pro Lys
    2765            2770            2775
Val Asp Ser Ser Leu Asp His Ile Ile Cys Thr Glu Pro Asp Leu
    2780            2785            2790
Ile Gly Lys Pro Ala Glu Glu Ser His Leu Ser Leu Ile Ala Ser
    2795            2800            2805
Val Thr Asp Lys Asp Pro Gln Gly Asn Gly Ser Asp Leu Ile Lys
    2810            2815            2820
Gly Arg Asp Gly Lys Ser Asp Ile Leu Ile Glu Asp Glu Thr Ser
    2825            2830            2835
Ile Gln Lys Met Tyr Leu Gly Glu Gly Glu Val Leu Val Glu Gly
    2840            2845            2850
Leu Val Glu Glu Glu Asn Arg His Leu Lys Leu Leu Pro Gly Lys
    2855            2860            2865
Asn Thr Arg Asp Ser Phe Lys Leu Ile Asn Ser Gln Phe Pro Phe
    2870            2875            2880
Pro Gln Ile Thr Asn Asn Glu Glu Leu Asn Gln Lys Gly Ser Leu
    2885            2890            2895
Lys Lys Ala Thr Val Thr Leu Lys Asp Glu Pro Asn Asn Leu Gln
    2900            2905            2910
Ile Ile Val Ser Lys Ser Pro Val Gln Phe Glu Asn Leu Glu Glu
    2915            2920            2925
Ile Phe Asp Thr Ser Val Ser Lys Glu Ile Ser Asp Asp Ile Thr
    2930            2935            2940
Ser Asp Ile Thr Ser Trp Glu Gly Asn Thr His Phe Glu Glu Ser
    2945            2950            2955
Phe Thr Asp Gly Pro Glu Lys Glu Leu Asp Leu Phe Thr Tyr Leu
    2960            2965            2970
Lys His Cys Ala Lys Asn Ile Lys Ala Lys Asp Val Ala Lys Pro
    2975            2980            2985
Asn Glu Asp Val Pro Ser His Val Leu Ile Thr Ala Pro Pro Met
    2990            2995            3000
Lys Glu His Leu Gln Leu Gly Val Asn Asn Thr Lys Glu Lys Ser
    3005            3010            3015
Thr Ser Thr Gln Lys Asp Ser Pro Leu Asn Asp Met Ile Gln Ser
    3020            3025            3030
Asn Asp Leu Cys Ser Lys Glu Ser Ile Ser Gly Gly Gly Thr Glu
    3035            3040            3045
Ile Ser Gln Phe Thr Pro Glu Ser Ile Glu Ala Thr Leu Ser Ile
    3050            3055            3060
Leu Ser Arg Lys His Val Glu Asp Val Gly Lys Asn Asp Phe Leu
    3065            3070            3075
Gln Ser Glu Arg Cys Ala Asn Gly Leu Gly Asn Asp Asn Ser Ser
    3080            3085            3090
Asn Thr Leu Asn Thr Asp Tyr Ser Phe Leu Glu Ile Asn Asn Lys
    3095            3100            3105
Lys Glu Arg Ile Glu Gln Gln Leu Pro Lys Glu Gln Ala Leu Ser
    3110            3115            3120
Pro Arg Ser Gln Glu Lys Glu Val Gln Ile Pro Glu Leu Ser Gln
    3125            3130            3135
Val Phe Val Glu Asp Val Lys Asp Ile Leu Lys Ser Arg Leu Lys
    3140            3145            3150
Glu Gly His Met Asn Pro Gln Glu Val Glu Pro Ser Ala Cys
```

-continued

```
            3155                3160                3165
Ala Asp Thr Lys Ile Leu Ile Gln Asn Leu Ile Lys Arg Ile Thr
            3170                3175                3180

Thr Ser Gln Leu Val Asn Glu Ala Ser Thr Val Pro Ser Asp Ser
            3185                3190                3195

Gln Met Ser Asp Ser Ser Gly Val Ser Pro Met Thr Asn Ser Ser
            3200                3205                3210

Glu Leu Lys Pro Glu Ser Arg Asp Asp Pro Phe Cys Ile Gly Asn
            3215                3220                3225

Leu Lys Ser Glu Leu Leu Leu Asn Ile Leu Lys Gln Asp Gln His
            3230                3235                3240

Ser Gln Lys Ile Thr Gly Val Phe Glu Leu Met Arg Glu Leu Thr
            3245                3250                3255

His Met Glu Tyr Asp Leu Glu Lys Arg Gly Ile Thr Ser Lys Val
            3260                3265                3270

Leu Pro Leu Gln Leu Glu Asn Ile Phe Tyr Lys Leu Leu Ala Asp
            3275                3280                3285

Gly Tyr Ser Glu Lys Ile Glu His Val Gly Asp Phe Asn Gln Lys
            3290                3295                3300

Ala Cys Ser Thr Ser Glu Met Met Glu Lys Pro His Ile Leu
            3305                3310                3315

Gly Asp Ile Lys Ser Lys Glu Gly Asn Tyr Tyr Ser Pro Asn Leu
            3320                3325                3330

Glu Thr Val Lys Glu Ile Gly Leu Glu Ser Ser Thr Val Trp Ala
            3335                3340                3345

Ser Thr Leu Pro Arg Asp Glu Lys Leu Lys Asp Leu Cys Asn Asp
            3350                3355                3360

Phe Pro Ser His Leu Glu Cys Thr Ser Gly Ser Lys Glu Met Ala
            3365                3370                3375

Ser Gly Asp Ser Ser Thr Glu Gln Phe Ser Ser Glu Leu Gln Gln
            3380                3385                3390

Cys Leu Gln His Thr Glu Lys Met His Glu Tyr Leu Thr Leu Leu
            3395                3400                3405

Gln Asp Met Lys Pro Pro Leu Asp Asn Gln Glu Ser Leu Asp Asn
            3410                3415                3420

Asn Leu Glu Ala Leu Lys Asn Gln Leu Arg Gln Leu Glu Thr Phe
            3425                3430                3435

Glu Leu Gly Leu Ala Pro Ile Ala Val Ile Leu Arg Lys Asp Met
            3440                3445                3450

Lys Leu Ala Glu Glu Phe Leu Lys Ser Leu Pro Ser Asp Phe Pro
            3455                3460                3465

Arg Gly His Val Glu Glu Leu Ser Ile Ser His Gln Ser Leu Lys
            3470                3475                3480

Thr Ala Phe Ser Ser Leu Ser Asn Val Ser Ser Glu Arg Thr Lys
            3485                3490                3495

Gln Ile Met Leu Ala Ile Asp Ser Glu Met Ser Lys Leu Ala Val
            3500                3505                3510

Ser His Glu Glu Phe Leu His Lys Leu Lys Ser Phe Ser Asp Trp
            3515                3520                3525

Val Ser Glu Lys Ser Lys Ser Val Lys Asp Ile Glu Ile Val Asn
            3530                3535                3540

Val Gln Asp Ser Glu Tyr Val Lys Lys Arg Leu Glu Phe Leu Lys
            3545                3550                3555
```

```
Asn Val Leu Lys Asp Leu Gly His Thr Lys Met Gln Leu Glu Thr
    3560            3565            3570

Thr Ala Phe Asp Val Gln Phe Phe Ile Ser Glu Tyr Ala Gln Asp
    3575            3580            3585

Leu Ser Pro Asn Gln Ser Lys Gln Leu Leu Arg Leu Leu Asn Thr
    3590            3595            3600

Thr Gln Lys Cys Phe Leu Asp Val Gln Glu Ser Val Thr Thr Gln
    3605            3610            3615

Val Glu Arg Leu Glu Thr Gln Leu His Leu Glu Gln Asp Leu Asp
    3620            3625            3630

Asp Gln Lys Ile Val Ala Glu Arg Gln Gln Glu Tyr Lys Glu Lys
    3635            3640            3645

Leu Gln Gly Ile Cys Asp Leu Leu Thr Gln Thr Glu Asn Arg Leu
    3650            3655            3660

Ile Gly His Gln Glu Ala Phe Met Ile Gly Asp Gly Thr Val Glu
    3665            3670            3675

Leu Lys Lys Tyr Gln Ser Lys Gln Glu Glu Leu Gln Lys Asp Met
    3680            3685            3690

Gln Gly Ser Ala Gln Ala Leu Ala Glu Val Val Lys Asn Thr Glu
    3695            3700            3705

Asn Phe Leu Lys Glu Asn Gly Glu Lys Leu Ser Gln Glu Asp Lys
    3710            3715            3720

Ala Leu Ile Glu Gln Lys Leu Asn Glu Ala Lys Ile Lys Cys Glu
    3725            3730            3735

Gln Leu Asn Leu Lys Ala Glu Gln Ser Lys Lys Glu Leu Asp Lys
    3740            3745            3750

Val Val Thr Thr Ala Ile Lys Glu Glu Thr Glu Lys Val Ala Ala
    3755            3760            3765

Val Lys Gln Leu Glu Glu Ser Lys Thr Lys Ile Glu Asn Leu Leu
    3770            3775            3780

Asp Trp Leu Ser Asn Val Asp Lys Asp Ser Glu Arg Ala Gly Thr
    3785            3790            3795

Lys His Lys Gln Val Ile Glu Gln Asn Gly Thr His Phe Gln Glu
    3800            3805            3810

Gly Asp Gly Lys Ser Ala Ile Gly Glu Glu Asp Glu Val Asn Gly
    3815            3820            3825

Asn Leu Leu Glu Thr Asp Val Asp Gly Gln Val Gly Thr Thr Gln
    3830            3835            3840

Glu Asn Leu Asn Gln Gln Tyr Gln Lys Val Lys Ala Gln His Glu
    3845            3850            3855

Lys Ile Ile Ser Gln His Gln Ala Val Ile Ile Ala Thr Gln Ser
    3860            3865            3870

Ala Gln Val Leu Leu Glu Lys Gln Gly Gln Tyr Leu Ser Pro Glu
    3875            3880            3885

Glu Lys Glu Lys Leu Gln Lys Asn Met Lys Glu Leu Lys Val His
    3890            3895            3900

Tyr Glu Thr Ala Leu Ala Glu Ser Glu Lys Lys Met Lys Leu Thr
    3905            3910            3915

His Ser Leu Gln Glu Glu Leu Glu Lys Phe Asp Ala Asp Tyr Thr
    3920            3925            3930

Glu Phe Glu His Trp Leu Gln Gln Ser Glu Gln Glu Leu Glu Asn
    3935            3940            3945
```

```
Leu Glu  Ala Gly Ala Asp Asp  Ile Asn Gly Leu Met  Thr Lys Leu
    3950             3955              3960

Lys Arg  Gln Lys Ser Phe Ser  Glu Asp Val Ile Ser  His Lys Gly
    3965             3970              3975

Asp Leu  Arg Tyr Ile Thr Ile  Ser Gly Asn Arg Val  Leu Glu Ala
    3980             3985              3990

Ala Lys  Ser Cys Ser Lys Arg  Asp Gly Gly Lys Val  Asp Thr Ser
    3995             4000              4005

Ala Thr  His Arg Glu Val Gln  Arg Lys Leu Asp His  Ala Thr Asp
    4010             4015              4020

Arg Phe  Arg Ser Leu Tyr Ser  Lys Cys Asn Val Leu  Gly Asn Asn
    4025             4030              4035

Leu Lys  Asp Leu Val Asp Lys  Tyr Gln His Tyr Glu  Asp Ala Ser
    4040             4045              4050

Cys Gly  Leu Leu Ala Gly Leu  Gln Ala Cys Glu Ala  Thr Ala Ser
    4055             4060              4065

Lys His  Leu Ser Glu Pro Ile  Ala Val Asp Pro Lys  Asn Leu Gln
    4070             4075              4080

Arg Gln  Leu Glu Glu Thr Lys  Ala Leu Gln Gly Gln  Ile Ser Ser
    4085             4090              4095

Gln Gln  Val Ala Val Glu Lys  Leu Lys Lys Thr Ala  Glu Val Leu
    4100             4105              4110

Leu Asp  Ala Arg Gly Ser Leu  Leu Pro Ala Lys Asn  Asp Ile Gln
    4115             4120              4125

Lys Thr  Leu Asp Asp Ile Val  Gly Arg Tyr Glu Asp  Leu Ser Lys
    4130             4135              4140

Ser Val  Asn Glu Arg Asn Glu  Lys Leu Gln Ile Thr  Leu Thr Arg
    4145             4150              4155

Ser Leu  Ser Val Gln Asp Gly  Leu Asp Glu Met Leu  Asp Trp Met
    4160             4165              4170

Gly Asn  Val Glu Ser Ser Leu  Lys Glu Gln Gly Gln  Val Pro Leu
    4175             4180              4185

Asn Ser  Thr Ala Leu Gln Asp  Ile Ile Ser Lys Asn  Ile Met Leu
    4190             4195              4200

Glu Gln  Asp Ile Ala Gly Arg  Gln Ser Ser Ile Asn  Ala Met Asn
    4205             4210              4215

Glu Lys  Val Lys Lys Phe Met  Glu Thr Thr Asp Pro  Ser Thr Ala
    4220             4225              4230

Ser Ser  Leu Gln Ala Lys Met  Lys Asp Leu Ser Ala  Arg Phe Ser
    4235             4240              4245

Glu Ala  Ser His Lys His Lys  Glu Thr Leu Ala Lys  Met Glu Glu
    4250             4255              4260

Leu Lys  Thr Lys Val Glu Leu  Phe Glu Asn Leu Ser  Glu Lys Leu
    4265             4270              4275

Gln Thr  Phe Leu Glu Thr Lys  Thr Gln Ala Leu Thr  Glu Val Asp
    4280             4285              4290

Val Pro  Gly Lys Asp Val Thr  Glu Leu Ser Gln Tyr  Met Gln Glu
    4295             4300              4305

Ser Thr  Ser Glu Phe Leu Glu  His Lys Lys His Leu  Glu Val Leu
    4310             4315              4320

His Ser  Leu Leu Lys Glu Ile  Ser Ser His Gly Leu  Pro Ser Asp
    4325             4330              4335

Lys Ala  Leu Val Leu Glu Lys  Thr Asn Asn Leu Ser  Lys Lys Phe
```

```
            4340            4345            4350
Lys Glu Met Glu Asp Thr Ile Lys Glu Lys Lys Glu Ala Val Thr
    4355            4360            4365
Ser Cys Gln Glu Gln Leu Asp Ala Phe Gln Val Leu Val Lys Ser
    4370            4375            4380
Leu Lys Ser Trp Ile Lys Glu Thr Thr Lys Lys Val Pro Ile Val
    4385            4390            4395
Gln Pro Ser Phe Gly Ala Glu Asp Leu Gly Lys Ser Leu Glu Asp
    4400            4405            4410
Thr Lys Lys Leu Gln Glu Lys Trp Ser Leu Lys Thr Pro Glu Ile
    4415            4420            4425
Gln Lys Val Asn Asn Ser Gly Ile Ser Leu Cys Asn Leu Ile Ser
    4430            4435            4440
Ala Val Thr Thr Pro Ala Lys Ala Ile Ala Ala Val Lys Ser Gly
    4445            4450            4455
Gly Ala Val Leu Asn Gly Glu Gly Thr Ala Thr Asn Thr Glu Glu
    4460            4465            4470
Phe Trp Ala Asn Lys Gly Leu Thr Ser Ile Lys Lys Asp Met Thr
    4475            4480            4485
Asp Ile Ser His Gly Tyr Glu Asp Leu Gly Leu Leu Leu Lys Asp
    4490            4495            4500
Lys Ile Ala Glu Leu Asn Thr Lys Leu Ser Lys Leu Gln Lys Ala
    4505            4510            4515
Gln Glu Glu Ser Ser Ala Met Met Gln Trp Leu Gln Lys Met Asn
    4520            4525            4530
Lys Thr Ala Thr Lys Trp Gln Gln Thr Pro Ala Pro Thr Asp Thr
    4535            4540            4545
Glu Ala Val Lys Thr Gln Val Glu Gln Asn Lys Ser Phe Glu Ala
    4550            4555            4560
Glu Leu Lys Gln Asn Val Asn Lys Val Gln Glu Leu Lys Asp Lys
    4565            4570            4575
Leu Thr Glu Leu Leu Glu Glu Asn Pro Asp Thr Pro Glu Ala Pro
    4580            4585            4590
Arg Trp Lys Gln Met Leu Thr Glu Ile Asp Ser Lys Trp Gln Glu
    4595            4600            4605
Leu Asn Gln Leu Thr Ile Asp Arg Gln Gln Lys Leu Glu Glu Ser
    4610            4615            4620
Ser Asn Asn Leu Thr Gln Phe Gln Thr Val Glu Ala Gln Leu Lys
    4625            4630            4635
Gln Trp Leu Val Glu Lys Glu Leu Met Val Ser Val Leu Gly Pro
    4640            4645            4650
Leu Ser Ile Asp Pro Asn Met Leu Asn Thr Gln Arg Gln Gln Val
    4655            4660            4665
Gln Ile Leu Leu Gln Glu Phe Ala Thr Arg Lys Pro Gln Tyr Glu
    4670            4675            4680
Gln Leu Thr Ala Ala Gly Gln Gly Ile Leu Ser Arg Pro Gly Glu
    4685            4690            4695
Asp Pro Ser Leu Arg Gly Ile Val Lys Glu Gln Leu Ala Ala Val
    4700            4705            4710
Thr Gln Lys Trp Asp Ser Leu Thr Gly Gln Leu Ser Asp Arg Cys
    4715            4720            4725
Asp Trp Ile Asp Gln Ala Ile Val Lys Ser Thr Gln Tyr Gln Ser
    4730            4735            4740
```

-continued

```
Leu Leu Arg Ser Leu Ser Asp Lys Leu Ser Asp Leu Asp Asn Lys
    4745                4750                4755

Leu Ser Ser Leu Ala Val Ser Thr His Pro Asp Ala Met Asn
    4760                4765                4770

Gln Gln Leu Glu Thr Ala Gln Lys Met Lys Gln Glu Ile Gln Gln
    4775                4780                4785

Glu Lys Lys Gln Ile Lys Val Ala Gln Ala Leu Cys Glu Asp Leu
    4790                4795                4800

Ser Ala Leu Val Lys Glu Glu Tyr Leu Lys Ala Glu Leu Ser Arg
    4805                4810                4815

Gln Leu Glu Gly Ile Leu Lys Ser Phe Lys Asp Val Glu Gln Lys
    4820                4825                4830

Ala Glu Asn His Val Gln His Leu Gln Ser Ala Cys Ala Ser Ser
    4835                4840                4845

His Gln Phe Gln Gln Met Ser Arg Asp Phe Gln Ala Trp Leu Asp
    4850                4855                4860

Thr Lys Lys Glu Glu Gln Asn Lys Ser His Pro Ile Ser Ala Lys
    4865                4870                4875

Leu Asp Val Leu Glu Ser Leu Ile Lys Asp His Lys Asp Phe Ser
    4880                4885                4890

Lys Thr Leu Thr Ala Gln Ser His Met Tyr Glu Lys Thr Ile Ala
    4895                4900                4905

Glu Gly Glu Asn Leu Leu Leu Lys Thr Gln Gly Ser Glu Lys Ala
    4910                4915                4920

Ala Leu Gln Leu Gln Leu Asn Thr Ile Lys Thr Asn Trp Asp Thr
    4925                4930                4935

Phe Asn Lys Gln Val Lys Glu Arg Glu Asn Lys Leu Lys Glu Ser
    4940                4945                4950

Leu Glu Lys Ala Leu Lys Tyr Lys Glu Gln Val Glu Thr Leu Trp
    4955                4960                4965

Pro Trp Ile Asp Lys Cys Gln Asn Asn Leu Glu Glu Ile Lys Phe
    4970                4975                4980

Cys Leu Asp Pro Ala Glu Gly Glu Asn Ser Ile Ala Lys Leu Lys
    4985                4990                4995

Ser Leu Gln Lys Glu Met Asp Gln His Phe Gly Met Val Glu Leu
    5000                5005                5010

Leu Asn Asn Thr Ala Asn Ser Leu Leu Ser Val Cys Glu Ile Asp
    5015                5020                5025

Lys Glu Val Val Thr Asp Glu Asn Lys Ser Leu Ile Gln Lys Val
    5030                5035                5040

Asp Met Val Thr Glu Gln Leu His Ser Lys Lys Phe Cys Leu Glu
    5045                5050                5055

Asn Met Thr Gln Lys Phe Lys Glu Phe Gln Glu Val Ser Lys Glu
    5060                5065                5070

Ser Lys Arg Gln Leu Gln Cys Ala Lys Glu Gln Leu Asp Ile His
    5075                5080                5085

Asp Ser Leu Gly Ser Gln Ala Tyr Ser Asn Lys Tyr Leu Thr Met
    5090                5095                5100

Leu Gln Thr Gln Gln Lys Ser Leu Gln Ala Leu Lys His Gln Val
    5105                5110                5115

Asp Leu Ala Lys Arg Leu Ala Gln Asp Leu Val Val Glu Ala Ser
    5120                5125                5130
```

```
Asp Ser Lys Gly Thr Ser Asp Val Leu Leu Gln Val Glu Thr Ile
5135                5140                5145

Ala Gln Glu His Ser Thr Leu Ser Gln Gln Val Asp Glu Lys Cys
5150                5155                5160

Ser Phe Leu Glu Thr Lys Leu Gln Gly Ile Gly His Phe Gln Asn
5165                5170                5175

Thr Ile Arg Glu Met Phe Ser Gln Phe Ala Glu Phe Asp Asp Glu
5180                5185                5190

Leu Asp Ser Met Ala Pro Val Gly Arg Asp Ala Glu Thr Leu Gln
5195                5200                5205

Lys Gln Lys Glu Thr Ile Lys Ala Phe Leu Lys Lys Leu Glu Ala
5210                5215                5220

Leu Met Ala Ser Asn Asp Asn Ala Asn Lys Thr Cys Lys Met Met
5225                5230                5235

Leu Ala Thr Glu Glu Thr Ser Pro Asp Leu Val Gly Ile Lys Arg
5240                5245                5250

Asp Leu Glu Ala Leu Ser Lys Gln Cys Asn Lys Leu Leu Asp Arg
5255                5260                5265

Ala Gln Ala Arg Glu Glu Gln Val Glu Gly Thr Ile Lys Arg Leu
5270                5275                5280

Glu Glu Phe Tyr Ser Lys Leu Lys Glu Phe Ser Ile Leu Leu Gln
5285                5290                5295

Lys Ala Glu Glu His Glu Glu Ser Gln Gly Pro Val Gly Met Glu
5300                5305                5310

Thr Glu Thr Ile Asn Gln Gln Leu Asn Met Phe Lys Val Phe Gln
5315                5320                5325

Lys Glu Glu Ile Glu Pro Leu Gln Gly Lys Gln Gln Asp Val Asn
5330                5335                5340

Trp Leu Gly Gln Gly Leu Ile Gln Ser Ala Ala Lys Ser Thr Ser
5345                5350                5355

Thr Gln Gly Leu Glu His Asp Leu Asp Asp Val Asn Ala Arg Trp
5360                5365                5370

Lys Thr Leu Asn Lys Lys Val Ala Gln Arg Ala Ala Gln Leu Gln
5375                5380                5385

Glu Ala Leu Leu His Cys Gly Arg Phe Gln Asp Ala Leu Glu Ser
5390                5395                5400

Leu Leu Ser Trp Met Val Asp Thr Glu Glu Leu Val Ala Asn Gln
5405                5410                5415

Lys Pro Pro Ser Ala Glu Phe Lys Val Val Lys Ala Gln Ile Gln
5420                5425                5430

Glu Gln Lys Leu Leu Gln Arg Leu Leu Asp Asp Arg Lys Ser Thr
5435                5440                5445

Val Glu Val Ile Lys Arg Glu Gly Glu Lys Ile Ala Thr Thr Ala
5450                5455                5460

Glu Pro Ala Asp Lys Val Lys Ile Leu Lys Gln Leu Ser Leu Leu
5465                5470                5475

Asp Ser Arg Trp Glu Ala Leu Leu Asn Lys Ala Glu Thr Arg Asn
5480                5485                5490

Arg Gln Leu Glu Gly Ile Ser Val Val Ala Gln Gln Phe His Glu
5495                5500                5505

Thr Leu Glu Pro Leu Asn Glu Trp Leu Thr Thr Ile Glu Lys Arg
5510                5515                5520

Leu Val Asn Cys Glu Pro Ile Gly Thr Gln Ala Ser Lys Leu Glu
```

```
            5525                5530                5535

Glu Gln Ile Ala Gln His Lys Ala Leu Glu Asp Ile Ile Asn
    5540            5545            5550

His Asn Lys His Leu His Gln Ala Val Ser Ile Gly Gln Ser Leu
    5555            5560            5565

Lys Val Leu Ser Ser Arg Glu Asp Lys Asp Met Val Gln Ser Lys
    5570            5575            5580

Leu Asp Phe Ser Gln Val Trp Tyr Ile Glu Ile Gln Glu Lys Ser
    5585            5590            5595

His Ser Arg Ser Glu Leu Leu Gln Gln Ala Leu Cys Asn Ala Lys
    5600            5605            5610

Ile Phe Gly Glu Asp Glu Val Glu Leu Met Asn Trp Leu Asn Glu
    5615            5620            5625

Val His Asp Lys Leu Ser Lys Leu Ser Val Gln Asp Tyr Ser Thr
    5630            5635            5640

Glu Gly Leu Trp Lys Gln Gln Ser Glu Leu Arg Val Leu Gln Glu
    5645            5650            5655

Asp Ile Leu Leu Arg Lys Gln Asn Val Asp Gln Ala Leu Leu Asn
    5660            5665            5670

Gly Leu Glu Leu Leu Lys Gln Thr Thr Gly Asp Glu Val Leu Ile
    5675            5680            5685

Ile Gln Asp Lys Leu Glu Ala Ile Lys Ala Arg Tyr Lys Asp Ile
    5690            5695            5700

Thr Lys Leu Ser Thr Asp Val Ala Lys Thr Leu Glu Gln Ala Leu
    5705            5710            5715

Gln Leu Ala Arg Arg Leu His Ser Thr His Glu Glu Leu Cys Thr
    5720            5725            5730

Trp Leu Asp Lys Val Glu Val Glu Leu Leu Ser Tyr Glu Thr Gln
    5735            5740            5745

Val Leu Lys Gly Glu Glu Ala Ser Gln Ala Gln Met Arg Pro Lys
    5750            5755            5760

Glu Leu Lys Lys Glu Ala Lys Asn Asn Lys Ala Leu Leu Asp Ser
    5765            5770            5775

Leu Asn Glu Val Ser Ser Ala Leu Leu Glu Leu Val Pro Trp Arg
    5780            5785            5790

Ala Arg Glu Gly Leu Glu Lys Met Val Ala Glu Asp Asn Glu Arg
    5795            5800            5805

Tyr Arg Leu Val Ser Asp Thr Ile Thr Gln Lys Val Glu Glu Ile
    5810            5815            5820

Asp Ala Ala Ile Leu Arg Ser Gln Gln Phe Asp Gln Ala Ala Asp
    5825            5830            5835

Ala Glu Leu Ser Trp Ile Thr Glu Thr Glu Lys Lys Leu Met Ser
    5840            5845            5850

Leu Gly Asp Ile Arg Leu Glu Gln Asp Gln Thr Ser Ala Gln Leu
    5855            5860            5865

Gln Val Gln Lys Thr Phe Thr Met Glu Ile Leu Arg His Lys Asp
    5870            5875            5880

Ile Ile Asp Asp Leu Val Lys Ser Gly His Lys Ile Met Thr Ala
    5885            5890            5895

Cys Ser Glu Glu Glu Lys Gln Ser Met Lys Lys Leu Asp Lys
    5900            5905            5910

Val Leu Lys Asn Tyr Asp Thr Ile Cys Gln Ile Asn Ser Glu Arg
    5915            5920            5925
```

-continued

| | | | | | | | | | | |
|---|---|---|---|---|---|---|---|---|---|---|
| Tyr | Leu | Gln | Leu | Glu | Arg | Ala | Gln | Ser | Leu | Val | Asn | Gln | Phe | Trp |
| | | 5930 | | | 5935 | | | | 5940 | | | |
| Glu | Thr | Tyr | Glu | Glu | Leu | Trp | Pro | Trp | Leu | Thr | Glu | Thr | Gln | Ser |
| | | 5945 | | | 5950 | | | | 5955 | | | |
| Ile | Ile | Ser | Gln | Leu | Pro | Ala | Pro | Ala | Leu | Glu | Tyr | Glu | Thr | Leu |
| | | 5960 | | | 5965 | | | | 5970 | | | |
| Arg | Gln | Gln | Gln | Glu | His | Arg | Gln | Leu | Arg | Glu | Leu | Ile | Ala |
| | | 5975 | | | 5980 | | | | 5985 | | | |
| Glu | His | Lys | Pro | His | Ile | Asp | Lys | Met | Asn | Lys | Thr | Gly | Pro | Gln |
| | | 5990 | | | 5995 | | | | 6000 | | | |
| Leu | Leu | Glu | Leu | Ser | Pro | Gly | Glu | Gly | Phe | Ser | Ile | Gln | Glu | Lys |
| | | 6005 | | | 6010 | | | | 6015 | | | |
| Tyr | Val | Ala | Ala | Asp | Thr | Leu | Tyr | Ser | Gln | Ile | Lys | Glu | Asp | Val |
| | | 6020 | | | 6025 | | | | 6030 | | | |
| Lys | Lys | Arg | Ala | Val | Ala | Leu | Asp | Glu | Ala | Ile | Ser | Gln | Ser | Thr |
| | | 6035 | | | 6040 | | | | 6045 | | | |
| Gln | Phe | His | Asp | Lys | Ile | Asp | Gln | Ile | Leu | Glu | Ser | Leu | Glu | Arg |
| | | 6050 | | | 6055 | | | | 6060 | | | |
| Ile | Val | Glu | Arg | Leu | Arg | Gln | Pro | Pro | Ser | Ile | Ser | Ala | Glu | Val |
| | | 6065 | | | 6070 | | | | 6075 | | | |
| Glu | Lys | Ile | Lys | Glu | Gln | Ile | Ser | Glu | Asn | Lys | Asn | Val | Ser | Val |
| | | 6080 | | | 6085 | | | | 6090 | | | |
| Asp | Met | Glu | Lys | Leu | Gln | Pro | Leu | Tyr | Glu | Thr | Leu | Lys | Gln | Arg |
| | | 6095 | | | 6100 | | | | 6105 | | | |
| Gly | Glu | Glu | Met | Ile | Ala | Arg | Ser | Gly | Thr | Asp | Lys | Asp | Ile |
| | | 6110 | | | 6115 | | | | 6120 | | | |
| Ser | Ala | Lys | Ala | Val | Gln | Asp | Lys | Leu | Asp | Gln | Met | Val | Phe | Ile |
| | | 6125 | | | 6130 | | | | 6135 | | | |
| Trp | Glu | Asn | Ile | His | Thr | Leu | Val | Glu | Glu | Arg | Glu | Ala | Lys | Leu |
| | | 6140 | | | 6145 | | | | 6150 | | | |
| Leu | Asp | Val | Met | Glu | Leu | Ala | Glu | Lys | Phe | Trp | Cys | Asp | His | Met |
| | | 6155 | | | 6160 | | | | 6165 | | | |
| Ser | Leu | Ile | Val | Thr | Ile | Lys | Asp | Thr | Gln | Asp | Phe | Ile | Arg | Asp |
| | | 6170 | | | 6175 | | | | 6180 | | | |
| Leu | Glu | Asp | Pro | Gly | Ile | Asp | Pro | Ser | Val | Val | Lys | Gln | Gln | Gln |
| | | 6185 | | | 6190 | | | | 6195 | | | |
| Glu | Ala | Ala | Glu | Thr | Ile | Arg | Glu | Glu | Ile | Asp | Gly | Leu | Gln | Glu |
| | | 6200 | | | 6205 | | | | 6210 | | | |
| Glu | Leu | Asp | Ile | Val | Ile | Asn | Leu | Gly | Ser | Glu | Leu | Ile | Ala | Ala |
| | | 6215 | | | 6220 | | | | 6225 | | | |
| Cys | Gly | Glu | Pro | Asp | Lys | Pro | Ile | Val | Lys | Lys | Ser | Ile | Asp | Glu |
| | | 6230 | | | 6235 | | | | 6240 | | | |
| Leu | Asn | Ser | Ala | Trp | Asp | Ser | Leu | Asn | Lys | Ala | Trp | Lys | Asp | Arg |
| | | 6245 | | | 6250 | | | | 6255 | | | |
| Ile | Asp | Lys | Leu | Glu | Glu | Ala | Met | Gln | Ala | Ala | Val | Gln | Tyr | Gln |
| | | 6260 | | | 6265 | | | | 6270 | | | |
| Asp | Gly | Leu | Gln | Ala | Val | Phe | Asp | Trp | Val | Asp | Ile | Ala | Gly | Gly |
| | | 6275 | | | 6280 | | | | 6285 | | | |
| Lys | Leu | Ala | Ser | Met | Ser | Pro | Ile | Gly | Thr | Asp | Leu | Glu | Thr | Val |
| | | 6290 | | | 6295 | | | | 6300 | | | |
| Lys | Gln | Gln | Ile | Glu | Glu | Leu | Lys | Gln | Phe | Lys | Ser | Glu | Ala | Tyr |
| | | 6305 | | | 6310 | | | | 6315 | | | |

```
Gln Gln Gln Ile Glu Met Glu Arg Leu Asn His Gln Ala Glu Leu
    6320                6325                6330

Leu Leu Lys Lys Val Thr Glu Glu Ser Asp Lys His Thr Val Gln
    6335                6340                6345

Asp Pro Leu Met Glu Leu Lys Leu Ile Trp Asp Ser Leu Glu Glu
    6350                6355                6360

Arg Ile Ile Asn Arg Gln His Lys Leu Glu Gly Ala Leu Leu Ala
    6365                6370                6375

Leu Gly Gln Phe Gln His Ala Leu Asp Glu Leu Leu Ala Trp Leu
    6380                6385                6390

Thr His Thr Glu Gly Leu Leu Ser Glu Gln Lys Pro Val Gly Gly
    6395                6400                6405

Asp Pro Lys Ala Ile Glu Ile Glu Leu Ala Lys His His Val Leu
    6410                6415                6420

Gln Asn Asp Val Leu Ala His Gln Ser Thr Val Glu Ala Val Asn
    6425                6430                6435

Lys Ala Gly Asn Asp Leu Ile Glu Ser Ser Ala Gly Glu Glu Ala
    6440                6445                6450

Ser Asn Leu Gln Asn Lys Leu Glu Val Leu Asn Gln Arg Trp Gln
    6455                6460                6465

Asn Val Leu Glu Lys Thr Glu Gln Arg Lys Gln Gln Leu Asp Gly
    6470                6475                6480

Ala Leu Arg Gln Ala Lys Gly Phe His Gly Glu Ile Glu Asp Leu
    6485                6490                6495

Gln Gln Trp Leu Thr Asp Thr Glu Arg His Leu Leu Ala Ser Lys
    6500                6505                6510

Pro Leu Gly Gly Leu Pro Glu Thr Ala Lys Glu Gln Leu Asn Val
    6515                6520                6525

His Met Glu Val Cys Ala Ala Phe Glu Ala Lys Glu Glu Thr Tyr
    6530                6535                6540

Lys Ser Leu Met Gln Lys Gly Gln Gln Met Leu Ala Arg Cys Pro
    6545                6550                6555

Lys Ser Ala Glu Thr Asn Ile Asp Gln Asp Ile Asn Asn Leu Lys
    6560                6565                6570

Glu Lys Trp Glu Ser Val Glu Thr Lys Leu Asn Glu Arg Lys Thr
    6575                6580                6585

Lys Leu Glu Glu Ala Leu Asn Leu Ala Met Glu Phe His Asn Ser
    6590                6595                6600

Leu Gln Asp Phe Ile Asn Trp Leu Thr Gln Ala Glu Gln Thr Leu
    6605                6610                6615

Asn Val Ala Ser Arg Pro Ser Leu Ile Leu Asp Thr Val Leu Phe
    6620                6625                6630

Gln Ile Asp Glu His Lys Val Phe Ala Asn Glu Val Asn Ser His
    6635                6640                6645

Arg Glu Gln Ile Ile Glu Leu Asp Lys Thr Gly Thr His Leu Lys
    6650                6655                6660

Tyr Phe Ser Gln Lys Gln Asp Val Val Leu Ile Lys Asn Leu Leu
    6665                6670                6675

Ile Ser Val Gln Ser Arg Trp Glu Lys Val Val Gln Arg Leu Val
    6680                6685                6690

Glu Arg Gly Arg Ser Leu Asp Asp Ala Arg Lys Arg Ala Lys Gln
    6695                6700                6705

Phe His Glu Ala Trp Ser Lys Leu Met Glu Trp Leu Glu Glu Ser
```

```
             6710              6715              6720
Glu Lys Ser Leu Asp Ser Glu Leu Glu Ile Ala Asn Asp Pro Asp
        6725              6730              6735
Lys Ile Lys Thr Gln Leu Ala Gln His Lys Glu Phe Gln Lys Ser
        6740              6745              6750
Leu Gly Ala Lys His Ser Val Tyr Asp Thr Thr Asn Arg Thr Gly
        6755              6760              6765
Arg Ser Leu Lys Glu Lys Thr Ser Leu Ala Asp Asp Asn Leu Lys
        6770              6775              6780
Leu Asp Asp Met Leu Ser Glu Leu Arg Asp Lys Trp Asp Thr Ile
        6785              6790              6795
Cys Gly Lys Ser Val Glu Arg Gln Asn Lys Leu Glu Glu Ala Leu
        6800              6805              6810
Leu Phe Ser Gly Gln Phe Thr Asp Ala Leu Gln Ala Leu Ile Asp
        6815              6820              6825
Trp Leu Tyr Arg Val Glu Pro Gln Leu Ala Glu Asp Gln Pro Val
        6830              6835              6840
His Gly Asp Ile Asp Leu Val Met Asn Leu Ile Asp Asn His Lys
        6845              6850              6855
Ala Phe Gln Lys Glu Leu Gly Lys Arg Thr Ser Ser Val Gln Ala
        6860              6865              6870
Leu Lys Arg Ser Ala Arg Glu Leu Ile Glu Gly Ser Arg Asp Asp
        6875              6880              6885
Ser Ser Trp Val Lys Val Gln Met Gln Glu Leu Ser Thr Arg Trp
        6890              6895              6900
Glu Thr Val Cys Ala Leu Ser Ile Ser Lys Gln Thr Arg Leu Glu
        6905              6910              6915
Ala Ala Leu Arg Gln Ala Glu Phe His Ser Val Val His Ala
        6920              6925              6930
Leu Leu Glu Trp Leu Ala Glu Ala Glu Gln Thr Leu Arg Phe His
        6935              6940              6945
Gly Val Leu Pro Asp Asp Glu Asp Ala Leu Arg Thr Leu Ile Asp
        6950              6955              6960
Gln His Lys Glu Phe Met Lys Lys Leu Glu Glu Lys Arg Ala Glu
        6965              6970              6975
Leu Asn Lys Ala Thr Thr Met Gly Asp Thr Val Leu Ala Ile Cys
        6980              6985              6990
His Pro Asp Ser Ile Thr Thr Ile Lys His Trp Ile Thr Ile Ile
        6995              7000              7005
Arg Ala Arg Phe Glu Glu Val Leu Ala Trp Ala Lys Gln His Gln
        7010              7015              7020
Gln Arg Leu Ala Ser Ala Leu Ala Gly Leu Ile Ala Lys Gln Glu
        7025              7030              7035
Leu Leu Glu Ala Leu Leu Ala Trp Leu Gln Trp Ala Glu Thr Thr
        7040              7045              7050
Leu Thr Asp Lys Asp Lys Glu Val Ile Pro Gln Glu Ile Glu Glu
        7055              7060              7065
Val Lys Ala Leu Ile Ala Glu His Gln Thr Phe Met Glu Glu Met
        7070              7075              7080
Thr Arg Lys Gln Pro Asp Val Asp Lys Val Thr Lys Thr Tyr Lys
        7085              7090              7095
Arg Arg Ala Ala Asp Pro Ser Ser Leu Gln Ser His Ile Pro Val
        7100              7105              7110
```

```
Leu Asp Lys Gly Arg Ala Gly Arg Lys Arg Phe Pro Ala Ser Ser
7115                 7120                7125

Leu Tyr Pro Ser Gly Ser Gln Thr Gln Ile Glu Thr Lys Asn Pro
7130                 7135                7140

Arg Val Asn Leu Leu Val Ser Lys Trp Gln Gln Val Trp Leu Leu
7145                 7150                7155

Ala Leu Glu Arg Arg Lys Leu Asn Asp Ala Leu Asp Arg Leu
7160                 7165                7170

Glu Glu Leu Arg Glu Phe Ala Asn Phe Asp Phe Asp Ile Trp Arg
7175                 7180                7185

Lys Lys Tyr Met Arg Trp Met Asn His Lys Lys Ser Arg Val Met
7190                 7195                7200

Asp Phe Phe Arg Arg Ile Asp Lys Asp Gln Asp Gly Lys Ile Thr
7205                 7210                7215

Arg Gln Glu Phe Ile Asp Gly Ile Leu Ser Ser Lys Phe Pro Thr
7220                 7225                7230

Ser Arg Leu Glu Met Ser Ala Val Ala Asp Ile Phe Asp Arg Asp
7235                 7240                7245

Gly Asp Gly Tyr Ile Asp Tyr Tyr Glu Phe Val Ala Ala Leu His
7250                 7255                7260

Pro Asn Lys Asp Ala Tyr Lys Pro Ile Thr Asp Ala Asp Lys Ile
7265                 7270                7275

Glu Asp Glu Val Thr Arg Gln Val Ala Lys Cys Lys Cys Ala Lys
7280                 7285                7290

Arg Phe Gln Val Glu Gln Ile Gly Asp Asn Lys Tyr Arg Phe Phe
7295                 7300                7305

Leu Gly Asn Gln Phe Gly Asp Ser Gln Gln Leu Arg Leu Val Arg
7310                 7315                7320

Ile Leu Arg Ser Thr Val Met Val Arg Val Gly Gly Trp Met
7325                 7330                7335

Ala Leu Asp Glu Phe Leu Val Lys Asn Asp Pro Cys Arg Val His
7340                 7345                7350

His His Gly Ser Lys Met Leu Arg Ser Glu Ser Asn Ser Ser Ile
7355                 7360                7365

Thr Thr Thr Gln Pro Thr Ile Ala Lys Gly Arg Thr Asn Met Glu
7370                 7375                7380

Leu Arg Glu Lys Phe Ile Leu Ala Asp Gly Ala Ser Gln Gly Met
7385                 7390                7395

Ala Ala Phe Arg Pro Arg Gly Arg Arg Ser Arg Pro Ser Ser Arg
7400                 7405                7410

Gly Ala Ser Pro Asn Arg Ser Thr Ser Val Ser Ser Gln Ala Ala
7415                 7420                7425

Gln Ala Ala Ser Pro Gln Val Pro Ala Thr Thr Pro Lys Gly
7430                 7435                7440

Thr Pro Ile Gln Gly Ser Lys Leu Arg Leu Pro Gly Tyr Leu Ser
7445                 7450                7455

Gly Lys Gly Phe His Ser Gly Glu Asp Ser Gly Leu Ile Thr Thr
7460                 7465                7470

Ala Ala Ala Arg Val Arg Thr Gln Phe Ala Asp Ser Lys Lys Thr
7475                 7480                7485

Pro Ser Arg Pro Gly Ser Arg Ala Gly Ser Lys Ala Gly Ser Arg
7490                 7495                7500
```

-continued

```
Ala Ser Ser Arg Arg Gly Ser Asp Ala Ser Asp Phe Asp Ile Ser
    7505                7510                7515

Glu Ile Gln Ser Val Cys Ser Asp Val Glu Thr Val Pro Gln Thr
    7520                7525                7530

His Arg Pro Thr Pro Arg Ala Gly Ser Arg Pro Ser Thr Ala Lys
    7535                7540                7545

Pro Ser Lys Ile Pro Thr Pro Gln Arg Lys Ser Pro Ala Ser Lys
    7550                7555                7560

Leu Asp Lys Ser Ser Lys Arg
    7565                7570

<210> SEQ ID NO 3
<211> LENGTH: 113
<212> TYPE: PRT
<213> ORGANISM: Homo sapiens

<400> SEQUENCE: 3

Met Asp Gly Arg Val Gln Leu Ile Lys Ala Leu Leu Ala Leu Pro Ile
1               5                   10                  15

Arg Pro Ala Thr Arg Arg Trp Arg Asn Pro Ile Pro Phe Pro Glu Thr
                20                  25                  30

Phe Asp Gly Asp Thr Asp Arg Leu Pro Glu Phe Ile Val Gln Thr Gly
            35                  40                  45

Ser Tyr Met Phe Val Asp Glu Asn Thr Phe Ser Ser Asp Ala Leu Lys
        50                  55                  60

Val Thr Phe Leu Ile Thr Arg Leu Thr Gly Pro Ala Leu Gln Trp Val
65                  70                  75                  80

Ile Pro Tyr Ile Lys Lys Glu Ser Pro Leu Leu Asn Asp Tyr Arg Gly
                85                  90                  95

Phe Leu Ala Glu Met Lys Arg Val Phe Gly Trp Glu Glu Asp Glu Asp
            100                 105                 110

Phe

<210> SEQ ID NO 4
<211> LENGTH: 113
<212> TYPE: PRT
<213> ORGANISM: Homo sapiens

<400> SEQUENCE: 4

Met Asp Gly Arg Val Gln Leu Met Lys Ala Leu Leu Ala Gly Pro Leu
1               5                   10                  15

Arg Pro Ala Ala Arg Arg Trp Arg Asn Pro Ile Pro Phe Pro Glu Thr
                20                  25                  30

Phe Asp Gly Asp Thr Asp Arg Leu Pro Glu Phe Ile Val Gln Thr Ser
            35                  40                  45

Ser Tyr Met Phe Val Asp Glu Asn Thr Phe Ser Asn Asp Ala Leu Lys
        50                  55                  60

Val Thr Phe Leu Ile Thr Arg Leu Thr Gly Pro Ala Leu Gln Trp Val
65                  70                  75                  80

Ile Pro Tyr Ile Arg Lys Glu Ser Pro Leu Leu Asn Asp Tyr Arg Gly
                85                  90                  95

Phe Leu Ala Glu Met Lys Arg Val Phe Gly Trp Glu Glu Asp Glu Asp
            100                 105                 110

Phe

<210> SEQ ID NO 5
```

<211> LENGTH: 113
<212> TYPE: PRT
<213> ORGANISM: Homo sapiens

<400> SEQUENCE: 5

Met Glu Gly Arg Val Gln Leu Met Lys Ala Leu Leu Ala Arg Pro Leu
1               5                   10                  15

Arg Pro Ala Ala Arg Arg Trp Arg Asn Pro Ile Pro Phe Pro Glu Thr
            20                  25                  30

Phe Asp Gly Asp Thr Asp Arg Leu Pro Glu Phe Ile Val Gln Thr Ser
        35                  40                  45

Ser Tyr Met Phe Val Asp Glu Asn Thr Phe Ser Asn Asp Ala Leu Lys
50                  55                  60

Val Thr Phe Leu Ile Thr Arg Leu Thr Gly Pro Ala Leu Gln Trp Val
65                  70                  75                  80

Ile Pro Tyr Ile Lys Lys Glu Ser Pro Leu Leu Ser Asp Tyr Arg Gly
                85                  90                  95

Phe Leu Ala Glu Met Lys Arg Val Phe Gly Trp Glu Glu Asp Glu Asp
            100                 105                 110

Phe

<210> SEQ ID NO 6
<211> LENGTH: 708
<212> TYPE: PRT
<213> ORGANISM: Homo sapiens

<400> SEQUENCE: 6

Met Thr Glu Arg Arg Arg Asp Glu Leu Ser Glu Glu Ile Asn Asn Leu
1               5                   10                  15

Arg Glu Lys Val Met Lys Gln Ser Glu Glu Asn Asn Asn Leu Gln Ser
            20                  25                  30

Gln Val Gln Lys Leu Thr Glu Glu Asn Thr Thr Leu Arg Glu Gln Val
        35                  40                  45

Glu Pro Thr Pro Glu Asp Glu Asp Asp Ile Glu Leu Arg Gly Ala
50                  55                  60

Ala Ala Ala Ala Pro Pro Pro Ile Glu Glu Cys Pro Glu
65                  70                  75                  80

Asp Leu Pro Glu Lys Phe Asp Gly Asn Pro Asp Met Leu Ala Pro Phe
            85                  90                  95

Met Ala Gln Cys Gln Ile Phe Met Glu Lys Ser Thr Arg Asp Phe Ser
            100                 105                 110

Val Asp Arg Val Arg Val Cys Phe Val Thr Ser Met Met Thr Gly Arg
            115                 120                 125

Ala Ala Arg Trp Ala Ser Ala Lys Leu Glu Arg Ser His Tyr Leu Met
        130                 135                 140

His Asn Tyr Pro Ala Phe Met Met Glu Met Lys His Val Phe Glu Asp
145                 150                 155                 160

Pro Gln Arg Arg Glu Val Ala Lys Arg Lys Ile Arg Arg Leu Arg Gln
                165                 170                 175

Gly Met Gly Ser Val Ile Asp Tyr Ser Asn Ala Phe Gln Met Ile Ala
            180                 185                 190

Gln Asp Leu Asp Trp Asn Glu Pro Ala Leu Ile Asp Gln Tyr His Glu
        195                 200                 205

Gly Leu Ser Asp His Ile Gln Glu Glu Leu Ser His Leu Glu Val Ala
    210                 215                 220

```
Lys Ser Leu Ser Ala Leu Ile Gly Gln Cys Ile His Ile Glu Arg Arg
225                 230                 235                 240

Leu Ala Arg Ala Ala Ala Arg Lys Pro Arg Ser Pro Pro Arg Ala
            245                 250                 255

Leu Val Leu Pro His Ile Ala Ser His His Gln Val Asp Pro Thr Glu
            260                 265                 270

Pro Val Gly Gly Ala Arg Met Arg Leu Thr Gln Glu Glu Lys Glu Arg
            275                 280                 285

Arg Arg Lys Leu Asn Leu Cys Leu Tyr Cys Gly Thr Gly Gly His Tyr
        290                 295                 300

Ala Asp Asn Cys Pro Ala Lys Ala Ser Lys Ser Ser Pro Ala Gly Lys
305                 310                 315                 320

Leu Pro Gly Pro Ala Val Glu Gly Pro Ser Ala Thr Gly Pro Glu Ile
            325                 330                 335

Ile Arg Ser Pro Gln Asp Asp Ala Ser Ser Pro His Leu Gln Val Met
            340                 345                 350

Leu Gln Ile His Leu Pro Gly Arg His Thr Leu Phe Val Arg Ala Met
        355                 360                 365

Ile Asp Ser Gly Ala Ser Gly Asn Phe Ile Asp His Glu Tyr Val Ala
370                 375                 380

Gln Asn Gly Ile Pro Leu Arg Ile Lys Asp Trp Pro Ile Leu Val Glu
385                 390                 395                 400

Ala Ile Asp Gly Arg Pro Ile Ala Ser Gly Pro Val Val His Glu Thr
            405                 410                 415

His Asp Leu Ile Val Asp Leu Gly Asp His Arg Glu Val Leu Ser Phe
            420                 425                 430

Asp Val Thr Gln Ser Pro Phe Phe Pro Val Val Leu Gly Val Arg Trp
            435                 440                 445

Leu Ser Thr His Asp Pro Asn Ile Thr Trp Ser Thr Arg Ser Ile Val
450                 455                 460

Phe Asp Ser Glu Tyr Cys Arg Tyr His Cys Arg Met Tyr Ser Pro Ile
465                 470                 475                 480

Pro Pro Ser Leu Pro Pro Ala Pro Gln Pro Pro Leu Tyr Tyr Pro
            485                 490                 495

Val Asp Gly Tyr Arg Val Tyr Gln Pro Val Arg Tyr Tyr Val Gln
            500                 505                 510

Asn Val Tyr Thr Pro Val Asp Glu His Val Tyr Pro Asp His Arg Leu
        515                 520                 525

Val Asp Pro His Ile Glu Met Ile Pro Gly Ala His Ser Ile Pro Ser
530                 535                 540

Gly His Val Tyr Ser Leu Ser Glu Pro Glu Met Ala Ala Leu Arg Asp
545                 550                 555                 560

Phe Val Ala Arg Asn Val Lys Asp Gly Leu Ile Thr Pro Thr Ile Ala
            565                 570                 575

Pro Asn Gly Ala Gln Val Leu Gln Val Lys Arg Gly Trp Lys Leu Gln
            580                 585                 590

Val Ser Tyr Asp Cys Arg Ala Pro Asn Asn Phe Thr Ile Gln Asn Gln
        595                 600                 605

Tyr Pro Arg Leu Ser Ile Pro Asn Leu Glu Asp Gln Ala His Leu Ala
        610                 615                 620

Thr Tyr Thr Glu Phe Val Pro Gln Ile Pro Gly Tyr Gln Thr Tyr Pro
625                 630                 635                 640

Thr Tyr Ala Ala Tyr Pro Thr Tyr Pro Val Gly Phe Ala Trp Tyr Pro
```

```
                    645                 650                 655
Val Gly Arg Asp Gly Gln Gly Arg Ser Leu Tyr Val Pro Val Met Ile
                660                 665                 670

Thr Trp Asn Pro His Trp Tyr Arg Gln Pro Pro Val Pro Gln Tyr Pro
            675                 680                 685

Pro Pro Gln Pro Pro Pro Pro Pro Pro Pro Pro Pro Pro Pro Pro Ser
        690                 695                 700

Tyr Ser Thr Leu
705

<210> SEQ ID NO 7
<211> LENGTH: 921
<212> TYPE: PRT
<213> ORGANISM: Homo sapiens

<400> SEQUENCE: 7

Met Ala Thr Pro Ser Ala Ala Phe Glu Ala Leu Met Asn Gly Val Thr
1               5                   10                  15

Ser Trp Asp Val Pro Glu Asp Ala Val Pro Cys Glu Leu Leu Leu Ile
            20                  25                  30

Gly Glu Ala Ser Phe Pro Val Met Val Asn Asp Met Gly Gln Val Leu
        35                  40                  45

Ile Ala Ala Ser Ser Tyr Gly Arg Gly Arg Leu Val Val Val Ser His
    50                  55                  60

Glu Asp Tyr Leu Val Glu Ala Gln Leu Thr Pro Phe Leu Leu Asn Ala
65                  70                  75                  80

Val Gly Trp Leu Cys Ser Ser Pro Gly Ala Pro Ile Gly Val His Pro
                85                  90                  95

Ser Leu Ala Pro Leu Ala Lys Ile Leu Glu Gly Ser Gly Val Asp Ala
            100                 105                 110

Lys Val Glu Pro Glu Val Lys Asp Ser Leu Gly Val Tyr Cys Ile Asp
        115                 120                 125

Ala Tyr Asn Glu Thr Met Thr Glu Lys Leu Val Lys Phe Met Lys Cys
    130                 135                 140

Gly Gly Gly Leu Leu Ile Gly Gly Gln Ala Trp Asp Trp Ala Asn Gln
145                 150                 155                 160

Gly Glu Asp Glu Arg Val Leu Phe Thr Phe Pro Gly Asn Leu Val Thr
                165                 170                 175

Ser Val Ala Gly Ile Tyr Phe Thr Asp Asn Lys Gly Asp Thr Ser Phe
            180                 185                 190

Phe Lys Val Ser Lys Lys Met Pro Lys Ile Pro Val Leu Val Ser Cys
        195                 200                 205

Glu Asp Asp Leu Ser Asp Arg Glu Glu Leu Leu His Gly Ile Ser
    210                 215                 220

Glu Leu Asp Ile Ser Asn Ser Asp Cys Phe Pro Ser Gln Leu Leu Val
225                 230                 235                 240

His Gly Ala Leu Ala Phe Pro Leu Gly Leu Asp Ser Tyr His Gly Cys
                245                 250                 255

Val Ile Ala Ala Ala Arg Tyr Gly Arg Gly Arg Val Val Val Thr Gly
            260                 265                 270

His Lys Val Leu Phe Thr Val Gly Lys Leu Gly Pro Phe Leu Leu Asn
        275                 280                 285

Ala Val Arg Trp Leu Asp Gly Gly Arg Arg Gly Lys Val Val Val Gln
    290                 295                 300
```

```
Thr Glu Leu Arg Thr Leu Ser Gly Leu Leu Ala Val Gly Gly Ile Asp
305                 310                 315                 320

Thr Ser Ile Glu Pro Asn Leu Thr Ser Asp Ala Ser Val Tyr Cys Phe
            325                 330                 335

Glu Pro Val Ser Glu Val Gly Val Lys Glu Leu Gln Glu Phe Val Ala
                340                 345                 350

Glu Gly Gly Gly Leu Phe Val Gly Ala Gln Ala Trp Trp Trp Ala Phe
        355                 360                 365

Lys Asn Pro Gly Val Ser Pro Leu Ala Arg Phe Pro Gly Asn Leu Leu
    370                 375                 380

Leu Asn Pro Phe Gly Ile Ser Ile Thr Ser Gln Ser Leu Asn Pro Gly
385                 390                 395                 400

Pro Phe Arg Thr Pro Lys Ala Gly Ile Arg Thr Tyr His Phe Arg Ser
                405                 410                 415

Thr Leu Ala Glu Phe Gln Val Ile Met Gly Arg Lys Arg Gly Asn Val
                420                 425                 430

Glu Lys Gly Trp Leu Ala Lys Leu Gly Pro Asp Gly Ala Ala Phe Leu
    435                 440                 445

Gln Ile Pro Ala Glu Ile Pro Ala Tyr Met Ser Val His Arg Leu
450                 455                 460

Leu Arg Lys Leu Leu Ser Arg Tyr Arg Leu Pro Val Ala Thr Arg Glu
465                 470                 475                 480

Asn Pro Val Ile Asn Asp Cys Cys Arg Gly Ala Met Leu Ser Leu Ala
                485                 490                 495

Thr Gly Leu Ala His Ser Gly Ser Asp Leu Ser Leu Val Pro Glu
        500                 505                 510

Ile Glu Asp Met Tyr Ser Ser Pro Tyr Leu Arg Pro Ser Glu Ser Pro
        515                 520                 525

Ile Thr Val Glu Val Asn Cys Thr Asn Pro Gly Thr Arg Tyr Cys Trp
        530                 535                 540

Met Ser Thr Gly Leu Tyr Ile Pro Gly Arg Gln Ile Ile Glu Val Ser
545                 550                 555                 560

Leu Pro Glu Ala Ala Ser Ala Asp Leu Lys Ile Gln Ile Gly Cys
                565                 570                 575

His Thr Asp Asp Leu Thr Arg Ala Ser Lys Leu Phe Arg Gly Pro Leu
            580                 585                 590

Val Ile Asn Arg Cys Cys Leu Asp Lys Pro Thr Lys Ser Ile Thr Cys
            595                 600                 605

Leu Trp Gly Gly Leu Leu Tyr Ile Ile Val Pro Gln Asn Ser Lys Leu
    610                 615                 620

Gly Ser Val Pro Val Thr Val Lys Gly Ala Val His Ala Pro Tyr Tyr
625                 630                 635                 640

Lys Leu Gly Glu Thr Thr Leu Glu Glu Trp Lys Arg Arg Ile Gln Glu
                645                 650                 655

Asn Pro Gly Pro Trp Gly Glu Leu Ala Thr Asp Asn Ile Ile Leu Thr
        660                 665                 670

Val Pro Thr Ala Asn Leu Arg Thr Leu Glu Asn Pro Glu Pro Leu Leu
    675                 680                 685

Arg Leu Trp Asp Glu Val Met Gln Ala Val Ala Arg Leu Gly Ala Glu
        690                 695                 700

Pro Phe Pro Leu Arg Leu Pro Gln Arg Ile Val Ala Asp Val Gln Ile
705                 710                 715                 720

Ser Val Gly Trp Met His Ala Gly Tyr Pro Ile Met Cys His Leu Glu
```

```
                725                 730                 735
Ser Val Gln Glu Leu Ile Asn Glu Lys Leu Ile Arg Thr Lys Gly Leu
            740                 745                 750

Trp Gly Pro Val His Glu Leu Gly Arg Asn Gln Gln Arg Gln Glu Trp
            755                 760                 765

Glu Phe Pro Pro His Thr Thr Glu Ala Thr Cys Asn Leu Trp Cys Val
        770                 775                 780

Tyr Val His Glu Thr Val Leu Gly Ile Pro Arg Ser Arg Ala Asn Ile
785                 790                 795                 800

Ala Leu Trp Pro Pro Val Arg Glu Lys Arg Val Arg Ile Tyr Leu Ser
                805                 810                 815

Lys Gly Pro Asn Val Lys Asn Trp Asn Ala Trp Thr Ala Leu Glu Thr
            820                 825                 830

Tyr Leu Gln Leu Gln Glu Ala Phe Gly Trp Glu Pro Phe Ile Arg Leu
            835                 840                 845

Phe Thr Glu Tyr Arg Asn Gln Thr Asn Leu Pro Thr Glu Asn Val Asp
        850                 855                 860

Lys Met Asn Leu Trp Val Lys Met Phe Ser His Gln Val Gln Lys Asn
865                 870                 875                 880

Leu Ala Pro Phe Phe Glu Ala Trp Ala Trp Pro Ile Gln Lys Glu Val
                885                 890                 895

Ala Thr Ser Leu Ala Tyr Leu Pro Glu Trp Lys Glu Asn Ile Met Lys
            900                 905                 910

Leu Tyr Leu Leu Thr Gln Met Pro His
            915                 920

<210> SEQ ID NO 8
<211> LENGTH: 370
<212> TYPE: PRT
<213> ORGANISM: Homo sapiens

<400> SEQUENCE: 8

Met Ser His Pro Ser Pro Gln Ala Lys Pro Ser Asn Pro Ser Asn Pro
1               5                   10                  15

Arg Val Phe Phe Asp Val Asp Ile Gly Gly Glu Arg Val Gly Arg Ile
            20                  25                  30

Val Leu Glu Leu Phe Ala Asp Ile Val Pro Lys Thr Ala Glu Asn Phe
        35                  40                  45

Arg Ala Leu Cys Thr Gly Glu Lys Gly Ile Gly His Thr Thr Gly Lys
    50                  55                  60

Pro Leu His Phe Lys Gly Cys Pro Phe His Arg Ile Ile Lys Lys Phe
65                  70                  75                  80

Met Ile Gln Gly Gly Asp Phe Ser Asn Gln Asn Gly Thr Gly Gly Glu
                85                  90                  95

Ser Ile Tyr Gly Glu Lys Phe Glu Asp Glu Asn Phe His Tyr Lys His
            100                 105                 110

Asp Arg Glu Gly Leu Leu Ser Met Ala Asn Ala Gly Arg Asn Thr Asn
        115                 120                 125

Gly Ser Gln Phe Phe Ile Thr Thr Val Pro Thr Pro His Leu Asp Gly
    130                 135                 140

Lys His Val Val Phe Gly Gln Val Ile Lys Gly Ile Gly Val Ala Arg
145                 150                 155                 160

Ile Leu Glu Asn Val Glu Val Lys Gly Glu Lys Pro Ala Lys Leu Cys
                165                 170                 175
```

```
Val Ile Ala Glu Cys Gly Glu Leu Lys Gly Asp Asp Gly Ile
            180                 185                 190

Phe Pro Lys Asp Gly Ser Gly Asp Ser His Pro Asp Phe Pro Glu Asp
            195                 200                 205

Ala Asp Ile Asp Leu Lys Asp Val Asp Lys Ile Leu Leu Ile Thr Glu
210                 215                 220

Asp Leu Lys Asn Ile Gly Asn Thr Phe Phe Lys Ser Gln Asn Trp Glu
225                 230                 235                 240

Met Ala Ile Lys Lys Tyr Ala Glu Val Leu Arg Tyr Val Asp Ser Ser
                245                 250                 255

Lys Ala Val Ile Glu Thr Ala Asp Arg Ala Lys Leu Gln Pro Ile Ala
            260                 265                 270

Leu Ser Cys Val Leu Asn Ile Gly Ala Cys Lys Leu Lys Met Ser Asn
        275                 280                 285

Trp Gln Gly Ala Ile Asp Ser Cys Leu Glu Ala Leu Glu Leu Asp Pro
    290                 295                 300

Ser Asn Thr Lys Ala Leu Tyr Arg Arg Ala Gln Gly Trp Gln Gly Leu
305                 310                 315                 320

Lys Glu Tyr Asp Gln Ala Leu Ala Asp Leu Lys Lys Ala Gln Gly Ile
                325                 330                 335

Ala Pro Glu Asp Lys Ala Ile Gln Ala Glu Leu Leu Lys Val Lys Gln
            340                 345                 350

Lys Ile Lys Ala Gln Lys Asp Lys Glu Lys Ala Val Tyr Ala Lys Met
        355                 360                 365

Phe Ala
    370

<210> SEQ ID NO 9
<211> LENGTH: 11
<212> TYPE: PRT
<213> ORGANISM: Homo sapiens

<400> SEQUENCE: 9

Val Asp Pro Leu Glu Thr Glu Leu Gly Val Lys
1               5                   10

<210> SEQ ID NO 10
<211> LENGTH: 16
<212> TYPE: PRT
<213> ORGANISM: Homo sapiens

<400> SEQUENCE: 10

Trp Gln Pro Gly Glu Glu Pro Ala Gly Ser Val Val Gln Asp Ser Arg
1               5                   10                  15

<210> SEQ ID NO 11
<211> LENGTH: 11
<212> TYPE: PRT
<213> ORGANISM: Homo sapiens

<400> SEQUENCE: 11

Glu Phe Ser Gln Ser Phe Asp Ala Ala Met Lys
1               5                   10

<210> SEQ ID NO 12
<211> LENGTH: 10
<212> TYPE: PRT
<213> ORGANISM: Homo sapiens

<400> SEQUENCE: 12
```

Thr Leu Glu Asn Pro Glu Pro Leu Leu Arg
1               5                   10

<210> SEQ ID NO 13
<211> LENGTH: 9
<212> TYPE: PRT
<213> ORGANISM: Homo sapiens

<400> SEQUENCE: 13

Leu Gly Ala Glu Pro Phe Pro Leu Arg
1               5

<210> SEQ ID NO 14
<211> LENGTH: 13
<212> TYPE: PRT
<213> ORGANISM: Homo sapiens

<400> SEQUENCE: 14

Glu Val Ala Thr Ser Leu Ala Tyr Leu Pro Glu Trp Lys
1               5                   10

<210> SEQ ID NO 15
<211> LENGTH: 9
<212> TYPE: PRT
<213> ORGANISM: Homo sapiens

<400> SEQUENCE: 15

His Val Val Phe Gly Gln Val Ile Lys
1               5

<210> SEQ ID NO 16
<211> LENGTH: 8
<212> TYPE: PRT
<213> ORGANISM: Homo sapiens

<400> SEQUENCE: 16

Asn Ile Gly Asn Thr Phe Phe Lys
1               5

<210> SEQ ID NO 17
<211> LENGTH: 11
<212> TYPE: PRT
<213> ORGANISM: Homo sapiens

<400> SEQUENCE: 17

Thr Ala Ile Glu Ser Phe Ala Leu Met Val Lys
1               5                   10

<210> SEQ ID NO 18
<211> LENGTH: 9
<212> TYPE: PRT
<213> ORGANISM: Homo sapiens

<400> SEQUENCE: 18

Met Glu Asp Phe Gln Ile Tyr Glu Lys
1               5

<210> SEQ ID NO 19
<211> LENGTH: 14
<212> TYPE: PRT
<213> ORGANISM: Homo sapiens

<400> SEQUENCE: 19

Glu Glu Val Tyr Ile Val Gln Ala Pro Thr Pro Glu Ile Lys

```
<210> SEQ ID NO 20
<211> LENGTH: 13
<212> TYPE: PRT
<213> ORGANISM: Homo sapiens

<400> SEQUENCE: 20

Ile Asn Glu Pro Gly Gln Ser Ala Val Phe Cys Gly Arg
1               5                   10

<210> SEQ ID NO 21
<211> LENGTH: 13
<212> TYPE: PRT
<213> ORGANISM: Homo sapiens

<400> SEQUENCE: 21

Phe Thr Val Tyr Pro Ile Met Pro Ala Ala Gly Pro Lys
1               5                   10

<210> SEQ ID NO 22
<211> LENGTH: 13
<212> TYPE: PRT
<213> ORGANISM: Homo sapiens

<400> SEQUENCE: 22

Glu Asn Thr Ala Tyr Phe Glu Phe Phe Asn Asp Ala Lys
1               5                   10

<210> SEQ ID NO 23
<211> LENGTH: 9
<212> TYPE: PRT
<213> ORGANISM: Homo sapiens

<400> SEQUENCE: 23

Val Leu Gln Glu Asp Ile Leu Leu Arg
1               5

<210> SEQ ID NO 24
<211> LENGTH: 12
<212> TYPE: PRT
<213> ORGANISM: Homo sapiens

<400> SEQUENCE: 24

Ser Glu Ala Tyr Gln Gln Gln Ile Glu Met Glu Arg
1               5                   10

<210> SEQ ID NO 25
<211> LENGTH: 11
<212> TYPE: PRT
<213> ORGANISM: Homo sapiens

<400> SEQUENCE: 25

Glu Val Ile Pro Gln Glu Ile Glu Glu Val Lys
1               5                   10

<210> SEQ ID NO 26
<211> LENGTH: 14
<212> TYPE: PRT
<213> ORGANISM: Homo sapiens

<400> SEQUENCE: 26

Val Gly Gly Gly Trp Met Ala Leu Asp Glu Phe Leu Val Lys
1               5                   10
```

-continued

<210> SEQ ID NO 27
<211> LENGTH: 13
<212> TYPE: PRT
<213> ORGANISM: Homo sapiens

<400> SEQUENCE: 27

Ser Leu Gly His Glu Val Asn Glu Leu Thr Ser Ser Arg
1               5                   10

<210> SEQ ID NO 28
<211> LENGTH: 11
<212> TYPE: PRT
<213> ORGANISM: Homo sapiens

<400> SEQUENCE: 28

Ser Leu Glu Gln Glu Thr Ser Gln Leu Glu Lys
1               5                   10

<210> SEQ ID NO 29
<211> LENGTH: 13
<212> TYPE: PRT
<213> ORGANISM: Homo sapiens

<400> SEQUENCE: 29

Ala Ser Ser Val Ile Ser Thr Ala Glu Gly Thr Thr Arg
1               5                   10

<210> SEQ ID NO 30
<211> LENGTH: 10
<212> TYPE: PRT
<213> ORGANISM: Homo sapiens

<400> SEQUENCE: 30

Gly Tyr Ser Phe Thr Thr Thr Ala Glu Arg
1               5                   10

<210> SEQ ID NO 31
<211> LENGTH: 11
<212> TYPE: PRT
<213> ORGANISM: Homo sapiens

<400> SEQUENCE: 31

Glu Ile Thr Ala Leu Ala Pro Ser Thr Met Lys
1               5                   10

<210> SEQ ID NO 32
<211> LENGTH: 17
<212> TYPE: PRT
<213> ORGANISM: Homo sapiens

<400> SEQUENCE: 32

Glu Gln Val Glu Pro Thr Pro Glu Asp Glu Asp Asp Ile Glu Leu
1               5                   10                  15

Arg

<210> SEQ ID NO 33
<211> LENGTH: 14
<212> TYPE: PRT
<213> ORGANISM: Homo sapiens

<400> SEQUENCE: 33

Trp Leu Ser Thr His Asp Pro Asn Ile Thr Trp Ser Thr Arg
1               5                   10

```
<210> SEQ ID NO 34
<211> LENGTH: 10
<212> TYPE: PRT
<213> ORGANISM: Homo sapiens

<400> SEQUENCE: 34

Ser Ile Val Phe Asp Ser Glu Tyr Cys Arg
1               5                   10

<210> SEQ ID NO 35
<211> LENGTH: 20
<212> TYPE: DNA
<213> ORGANISM: Artificial Sequence
<220> FEATURE:
<223> OTHER INFORMATION: UBE3A sense LNA

<400> SEQUENCE: 35
tttacaccta cttcttaaca                                               20

<210> SEQ ID NO 36
<211> LENGTH: 20
<212> TYPE: DNA
<213> ORGANISM: Artificial Sequence
<220> FEATURE:
<223> OTHER INFORMATION: Antisense LNA

<400> SEQUENCE: 36
ctttccattt atttccattt                                               20
```

E3 UBIQUITIN LIGASE (UBE3A) PROTEIN TARGETS

This patent application is a U.S. national phase of International Application No. PCT/EP2020/050861 filed on Jan. 15, 2020, which claims the benefit and priority of European Patent Application No. 19152337.2, filed on Jan. 17, 2019, the disclosure of which is incorporated by reference herein in its entirety.

The present invention provides novel biomarkers whose protein expression levels are modulated when ubiquitin-protein ligase E3A (UBE3A) protein levels are increased or decreased and their use in drug development.

BACKGROUND OF INVENTION

Angelman syndrome is characterized by severe intellectual and developmental disability, sleep disturbance, seizures, jerky movements, EEG abnormalities, frequent laughter or smiling, and profound language impairments. Angelman syndrome is neuro-genetic disorder caused by deletion or inactivation of the UBE3A genes and thus protein on the maternally inherited chromosome 15q11.2. Conversely, Dup15q Syndrome is a clinically identifiable syndrome which results from duplications of chromosome 15q11-13.1. In Dup15q Syndrome there is an overexpression of UBE3A. In Angelman syndrome (AS) the neuronal loss of E3 Ubiquitin ligase UBE3A leads to a plethora of severe neurological disabilities.

Although neuronal loss of UBE3A causes AS, there is a paucity of knowledge of downstream molecular and cellular dysfunction. Identification of relevant UBE3A substrates, will lead to a better understanding of the role of Ube3a function in health and disease, and support both drug and biomarker discovery to monitor UBE3A function.

SUMMARY OF THE INVENTION

The present invention relates to novel biomarkers whose protein expression is modulated when ubiquitin-protein ligase E3A (UBE3A) protein levels are increased or decreased and furthermore some are forming a protein complex with UBE3A. These include proteins CCDC88A, DST, FAM127A, FAM127B, FAM127C, PEG10, TCAF1 and PPID. FAM127A, FAM127B, FAM127C, PEG10 are LTR retrotransposon-derived genes containing GAG capsid domains and PEG10 is found in exosomes. The present invention further relates to pharmaceutical biomarkers and methods the detection of UBE3A activity based on these proteins for pharmaceutical treatment for diseases targeting UBE3A including Angelman syndrome, 15qdup syndrome and other Autism Spectrum Disorders.

SHORT DESCRIPTION OF THE FIGURES

FIG. 1: Identification of novel Ube3a targets including proteins CCDC88A, DST, FAM127A, FAM127B, FAM127C, PEG10, TCAF1 and PPID.

FIG. 1A: Schematic of the experimental design of neuronal differentiation starting with Control (Control 1) and AS lines (Patient 1,3) with UBE3A sense targeting LNA (Sense) treatment on Control lines and UBE3A ATS targeting LNA treatment on AS lines for 2 weeks or 6 weeks over the course of neuronal differentiation.

Figure 1B:
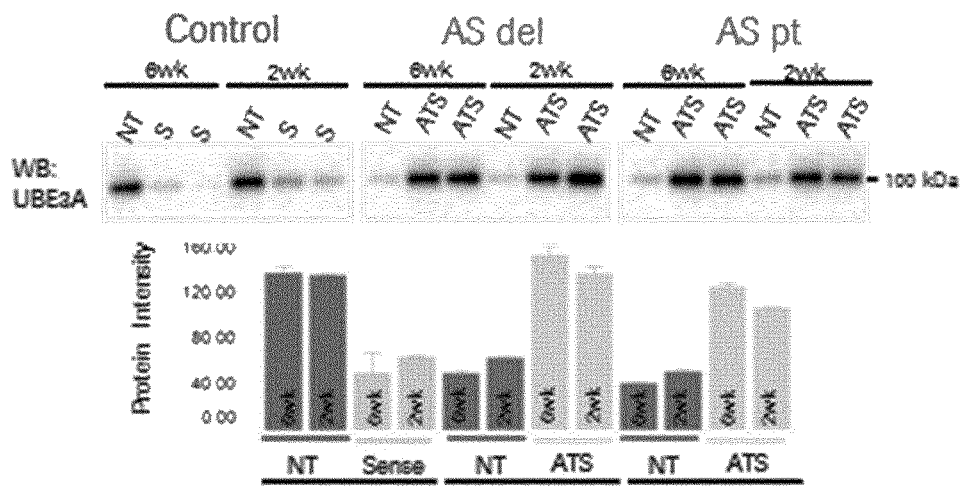

FIG. 1B: Western blotting (top) for UBE3A on cell lysates used for TMT-MS3 experiment. UBE3A scaled abundance plots obtained from Proteome Discoverer with 2 and 6 weeks of LNA treatment reveals UBE3A knockdown and reinstatement upon LNA treatment.

Figure 1C:
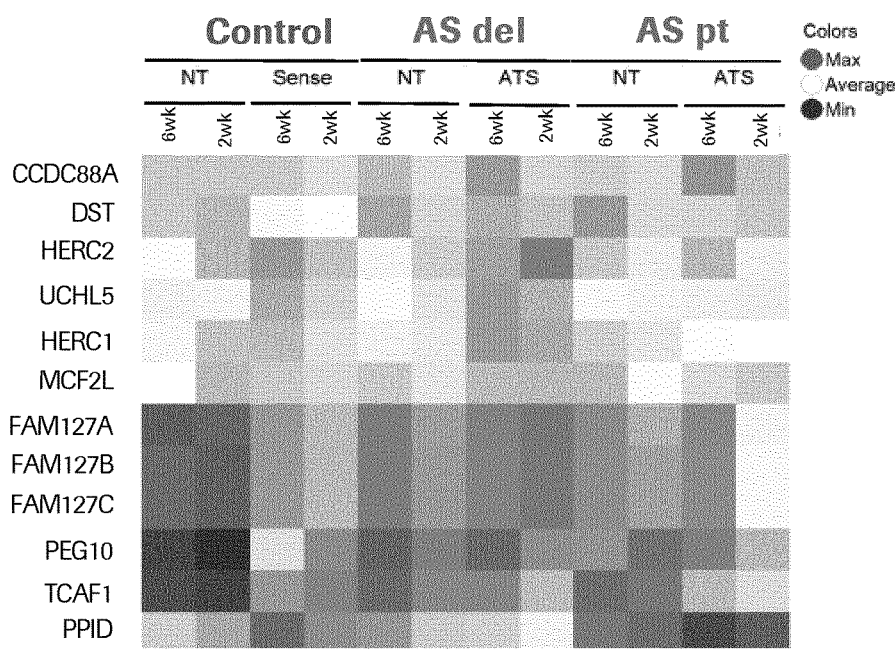

FIG. 1C: Heatmap of Scaled abundances of proteins inversely modulated with respect to UBE3A levels in Control and AS lines (AS del, AS pt).

Figure 2:
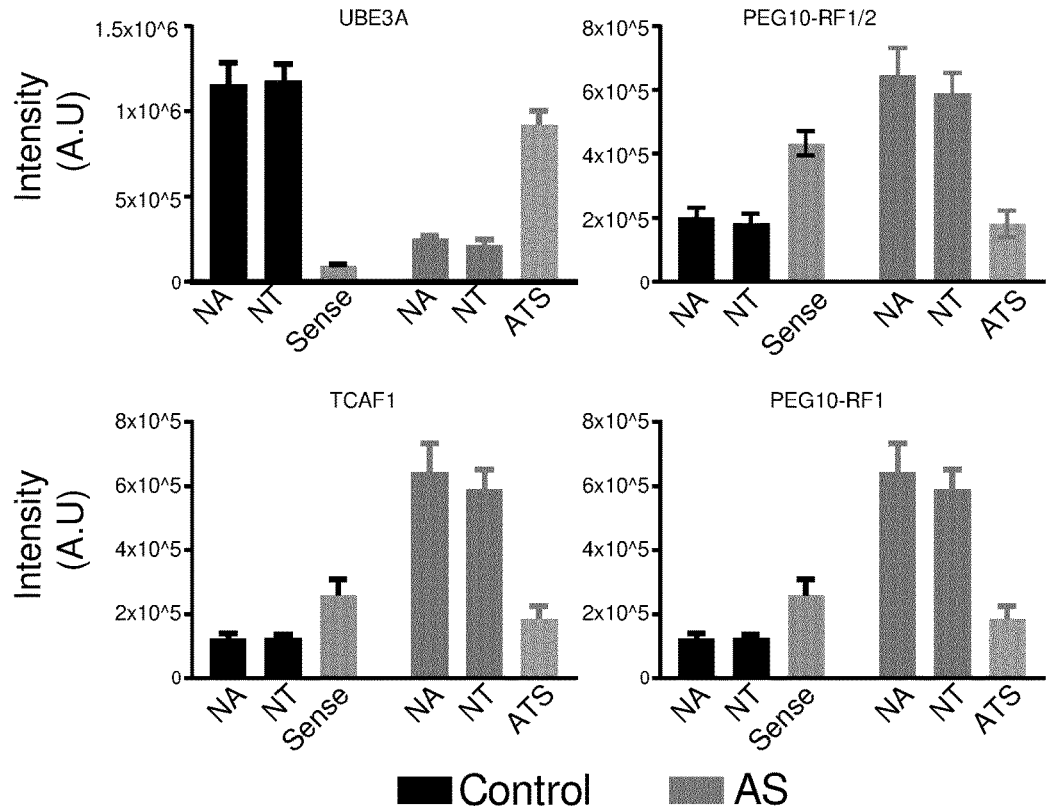

FIG. 2: Confirmation of PEG 10 and TCAF1 as UBE3A target by SRM

SRM quantification of UBE3A, PEG10 RF1/2 specific peptide, PEG10-RF1 peptide and TCAF1 in control and AS cells. NA refers to no treatment, NT refers to non-targeting LNA treatment, Sense: UBE3A sense LNA treatment and ATS: UBE3A ATS LNA treatment. (n=2 lines for control, n=3 for AS, 3 differentiations each).

Figure 3:
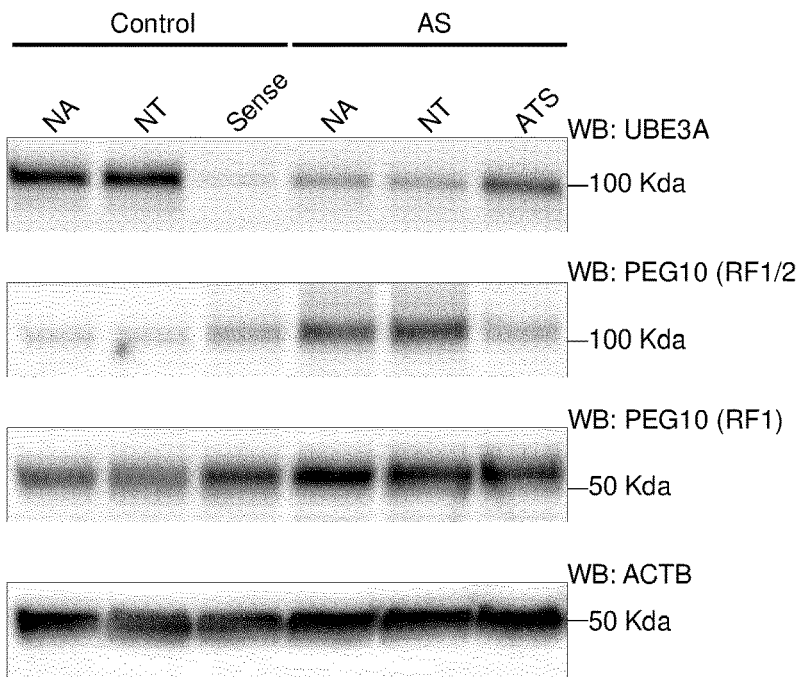

FIG. 3: Confirmation of PEG 10 as UBE3A target by Western. Western blotting for UBE3A, PEG10 and ACTB in lysates of Control and AS neurons with either no treatment (NA), Non targeting LNA treatment (NT) and Sense/ATS treatment respectively shows robust UBE3A dependent inverse relationship for PEG10 RF1/2 isoform.

Figure 4A:
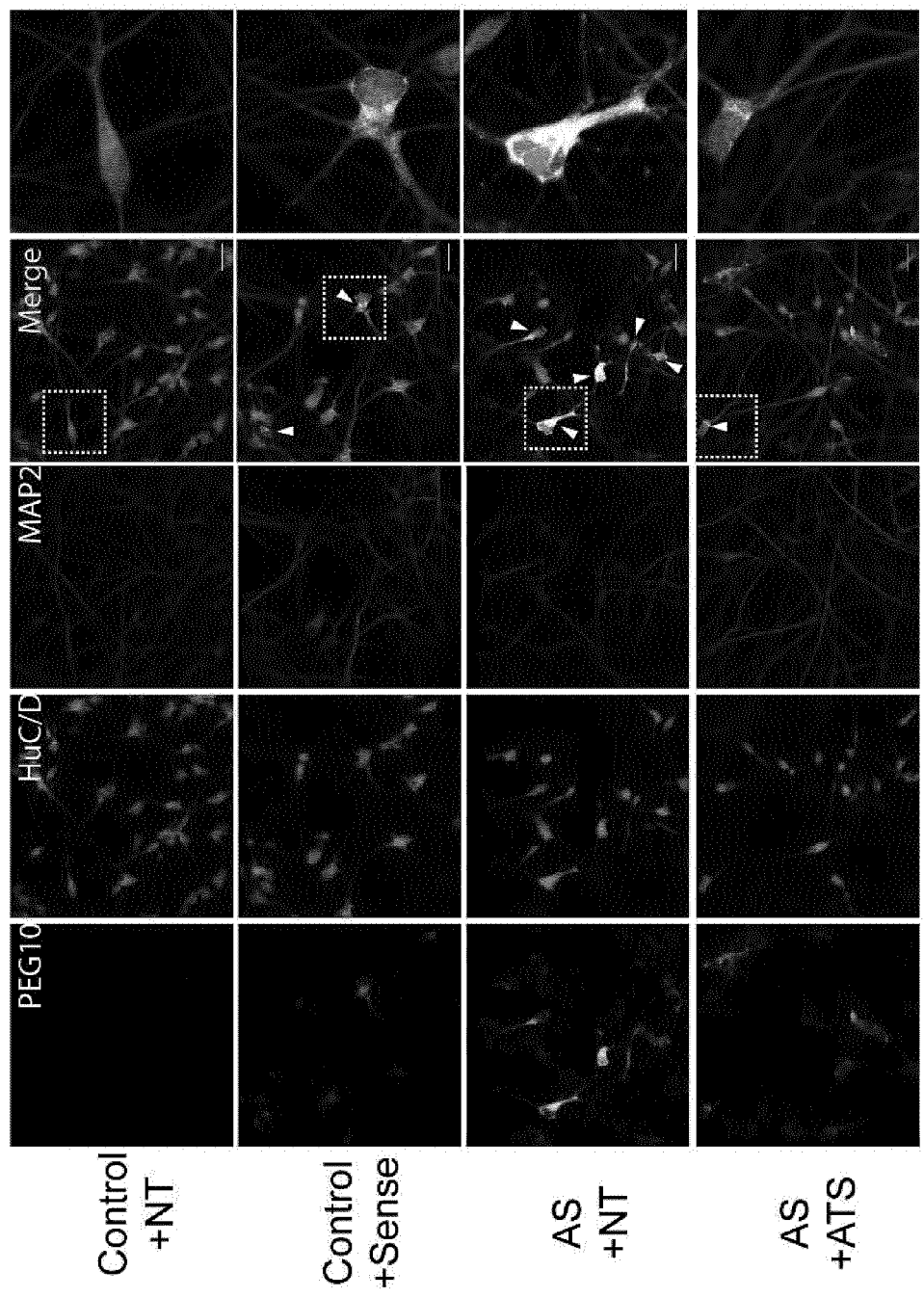

FIG. 4A: Representative immunostainings for PEG10 RF1/2 in control and AS neurons with UBE3A knockdown (Sense) in Control neurons and UBE3A reinstatement (ATS) in AS neurons.

Figure 4B:
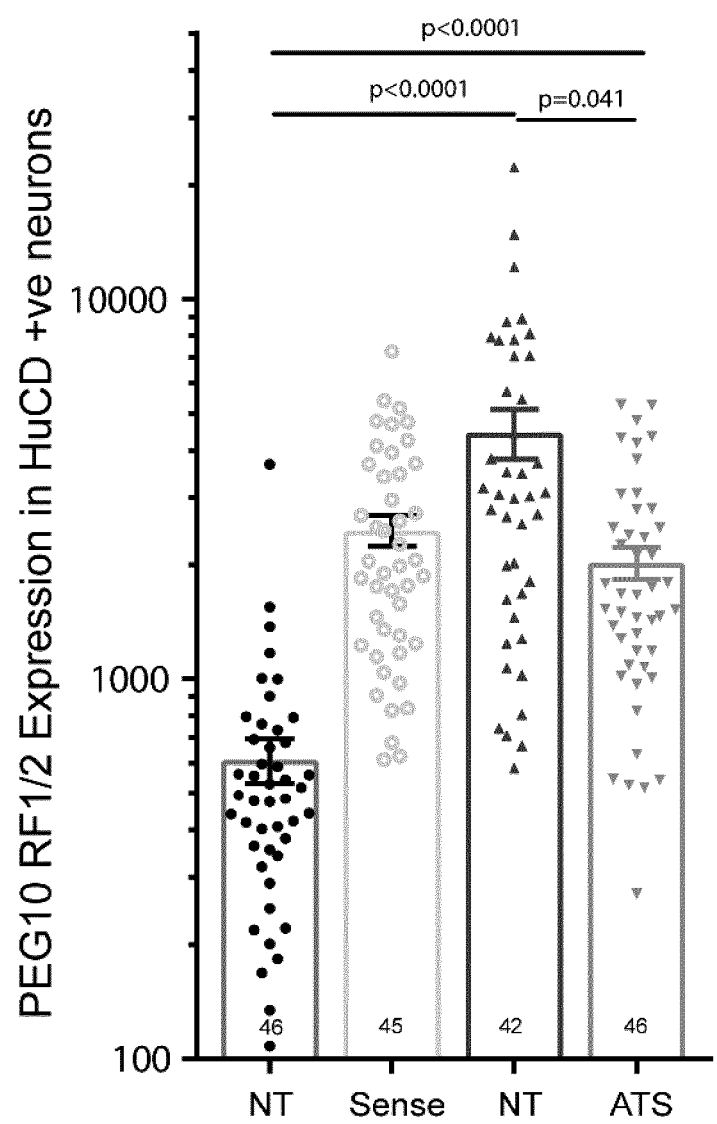

FIG. 4B: Quantification of PEG10 intensities in Control and AS HuCD positive neurons in Control and AS neurons (data points are individual neurons from two independent neuronal differentiations of control and AS cells, P values are adjusted for multiple comparisons based on Dunn's multiple comparison test).

Figure 5A:
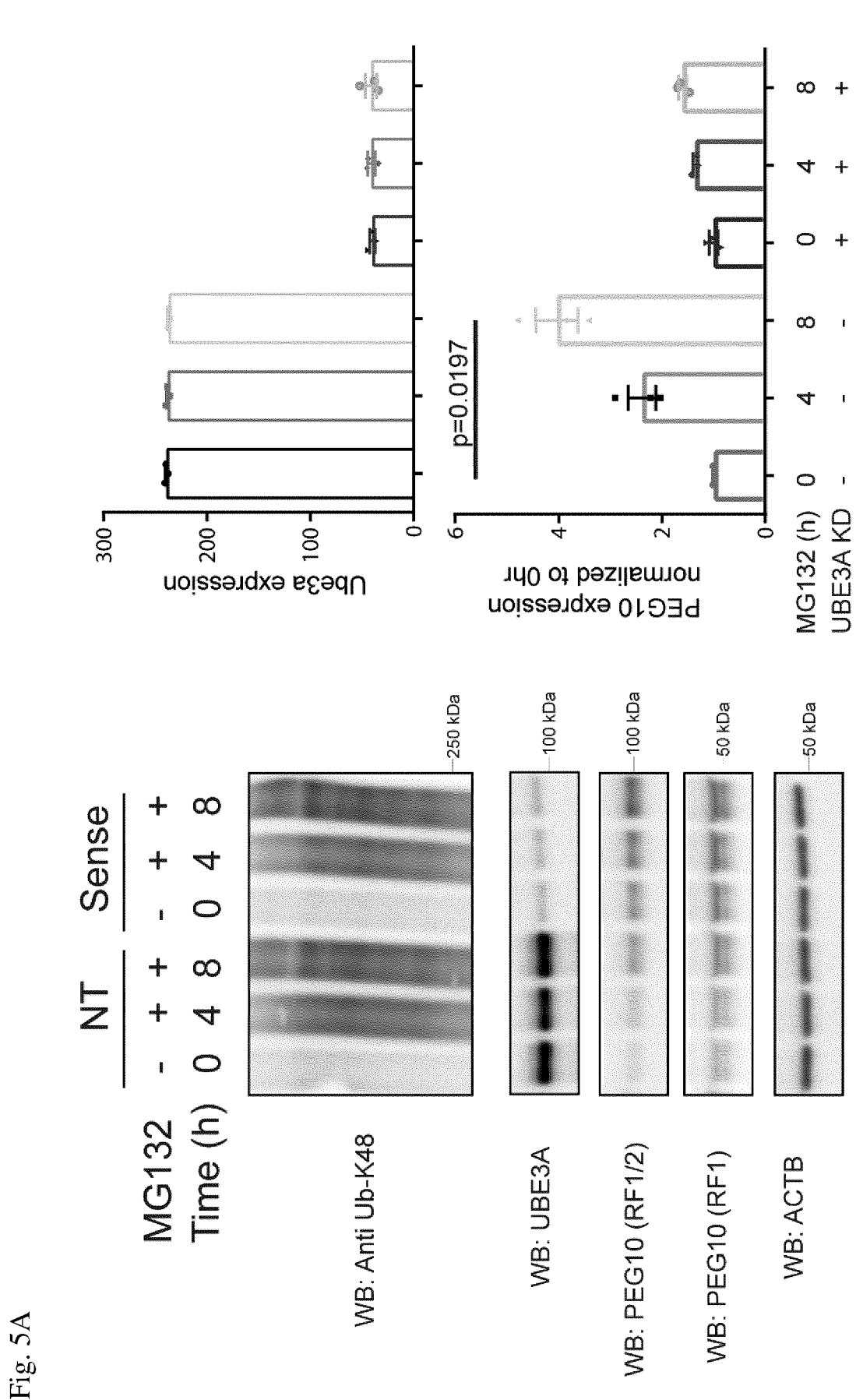

FIG. 5A: Left: Western blotting analysis of UBE3A and PEG10 expression under time course of proteasome inhibition (MG132, 10 mM) with and without UBE3A knockdown (Sense) at 0, 4 and 8 hours. Right: Quantification of UBE3A and PEG10 RF1/2 expression with proteasome inhibition. (n=3 independent experiments, P values: Dunn's multiple comparison test, adjusted for multiple testing).

Figure 5B:
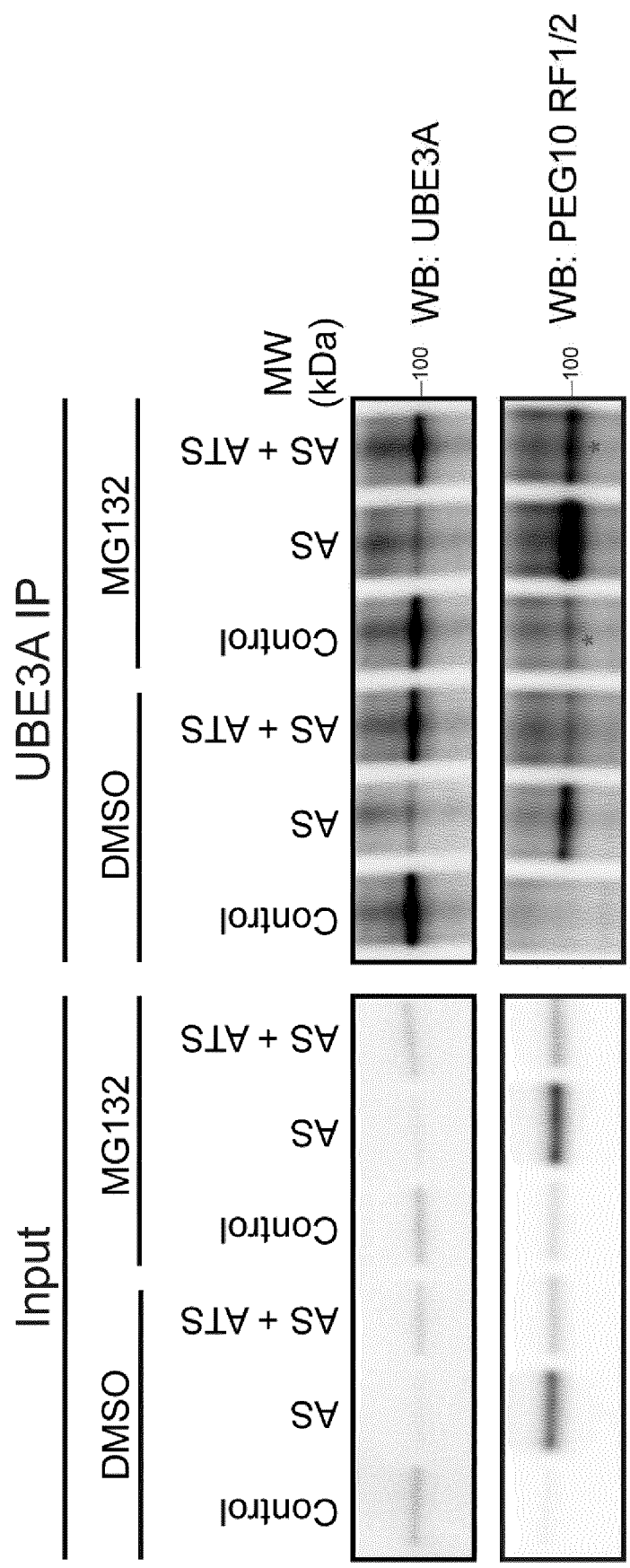

FIG. 5B: Western blotting analysis of UBE3A IP under proteasome inhibition (MG132, 10 mM, 6 h) treatment in Control, AS and AS+ATS treatment. Red dots represent PEG10-UBE3A complex stabilized by MG132 treatment.

Figure 5C:
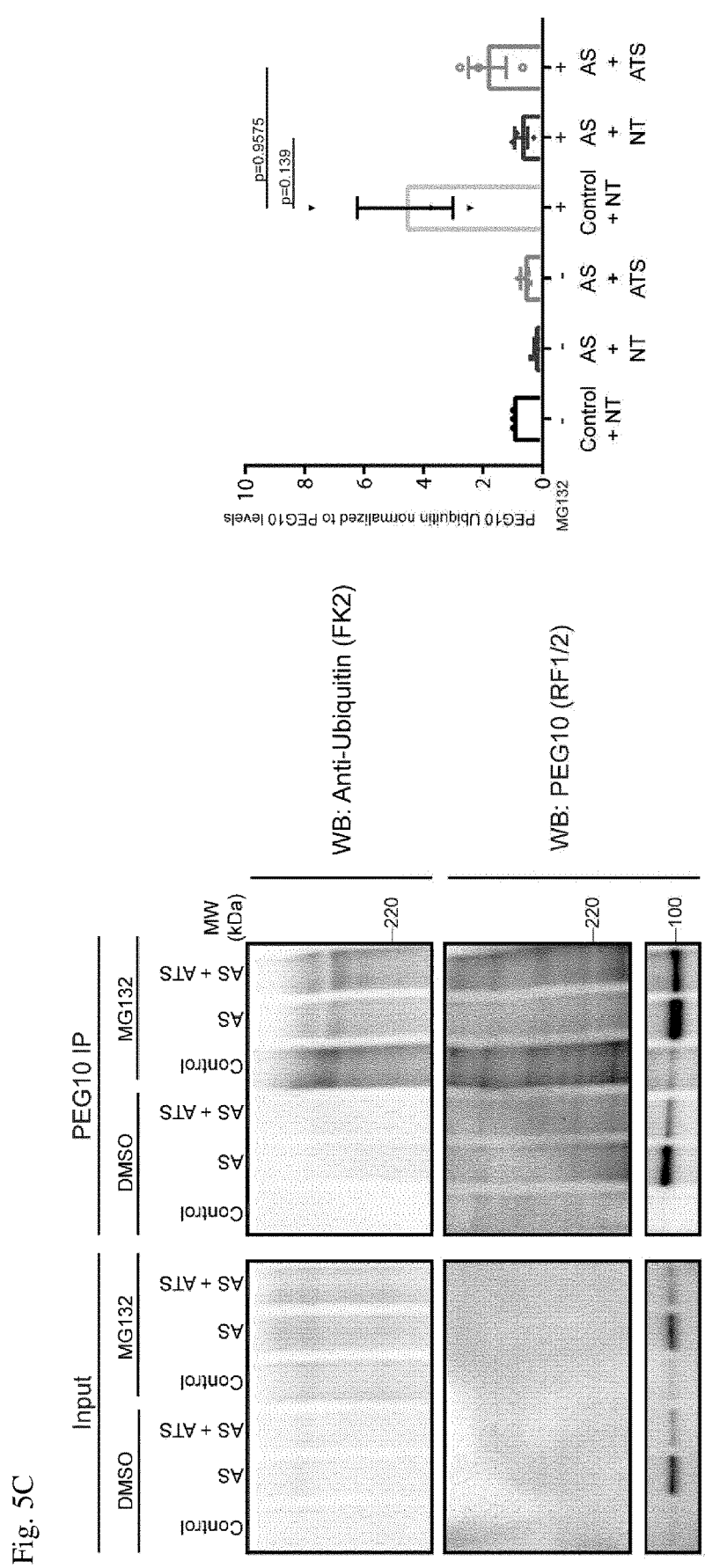

FIG. 5C: Left: Western blotting analysis of PEG10 ubiquitination with PEG10 IP in Control, AS, AS+ATS treatment with proteasome inhibition (MG132, 10 mM, 6 h). Right: Quantification of PEG10 ubiquitination. (n=3 independent experiments, P values: Dunn's multiple comparison test, adjusted for multiple testing,).

Figure 6A:
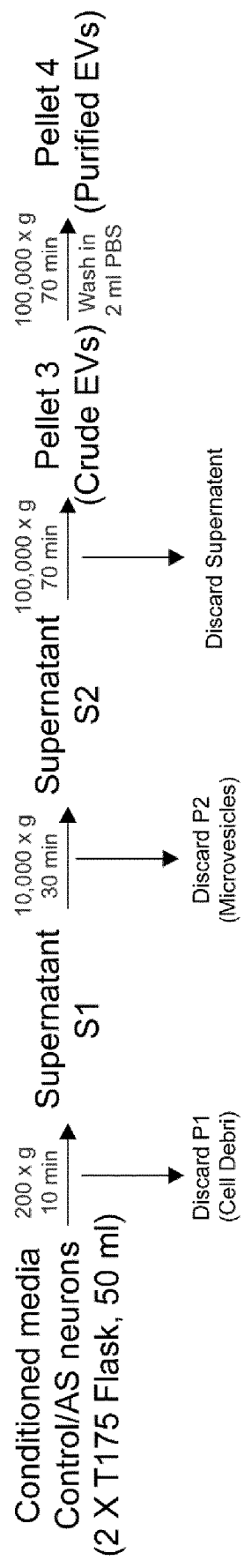

FIG. 6A: Scheme for isolation of extracellular vesicles (EVs) from IPSC neurons.

Figure 6B:
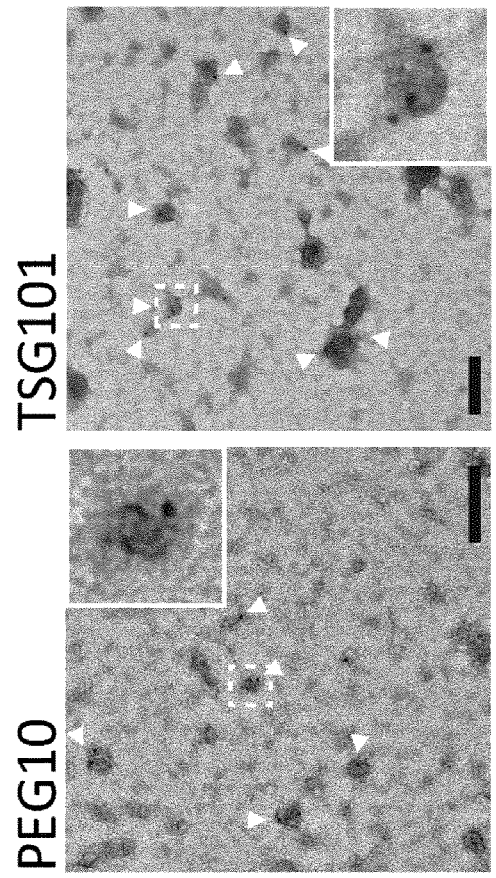

FIG. 6B: Representative Immuno-EM measurements for PEG10 RF1/2 and TSG101 in Evs from AS cells (Magnification: 15,000, Insert 4× zoom, Scale bar: 200 nm).

Figure 6C:
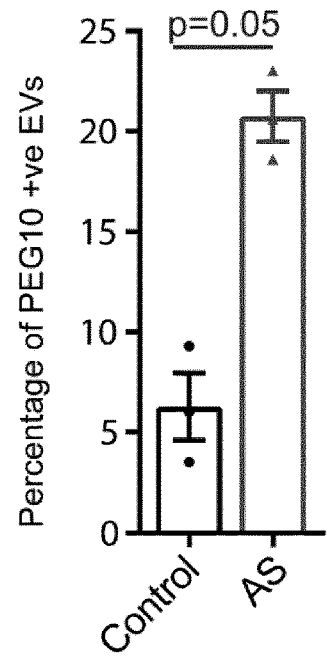

FIG. 6C: Quantification of PEG10 RF1/2 positive Evs from Control and AS cells (n=3 independent EV preparations, p value: Mann-Whitney test).

Figure 6D:
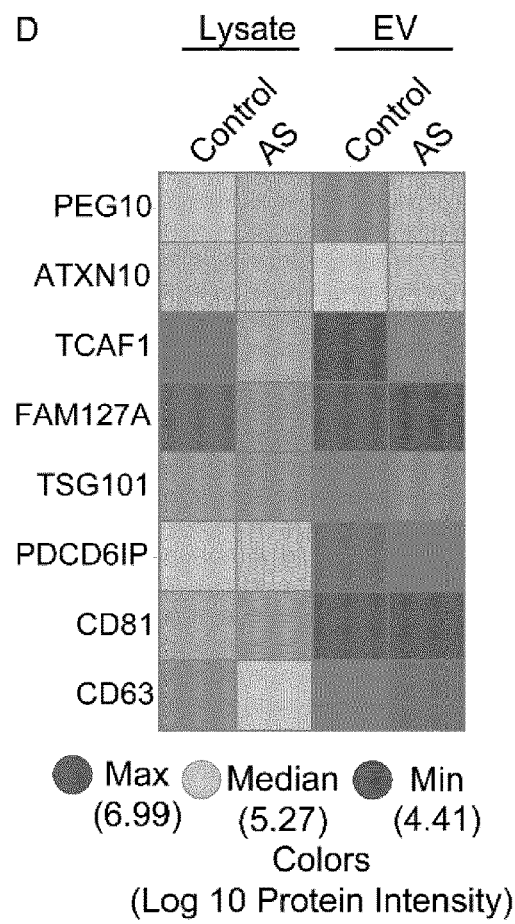

FIG. 6D: LC-MS heatmap for PEG10 and its binding proteins and selected EV markers in Control and AS lysates (values are gene level intensities obtained from Spectronaut and are averages of 3 independent lysate and EV preparations).

Figure 6E:
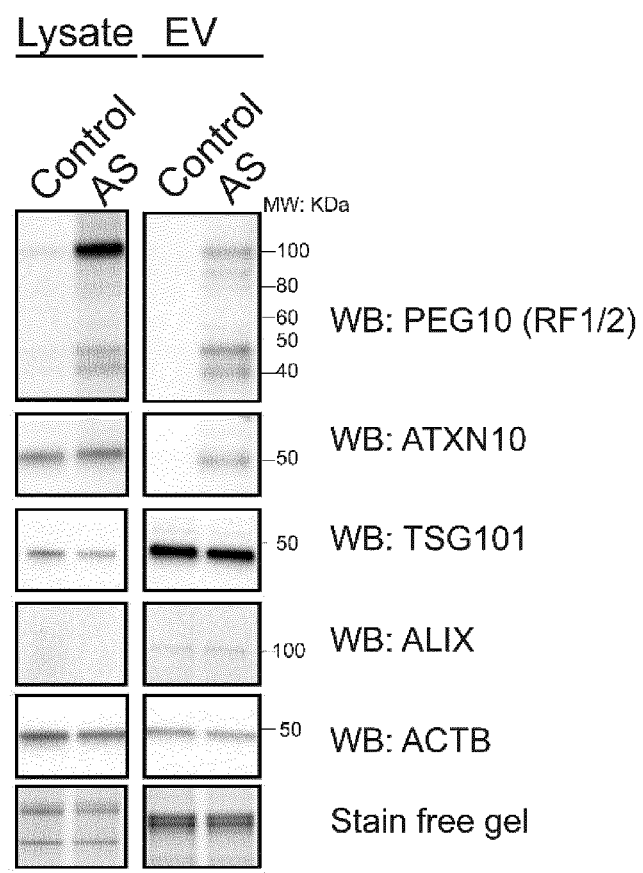

FIG. 6E: Immunoblotting analysis for PEG10 RF1/2 and ATXN10 along with EV markers with equal total protein loaded for lysates and Evs.

DETAILED DESCRIPTION OF THE INVENTION

In a first aspect, the present invention provides a method for measuring UBE3A protein expression modulation in a tissue sample comprising the steps:

a) providing a tissue sample of an animal or cell culture which has been treated with a UBE3A modulator,
b) measuring a protein expression level in the sample of step a) of at least one protein selected from the group consisting of: CCDC88A, DST, FAM127A, FAM127B, FAM127C, PEG10 and TCAF1, PPID.
c) comparing the protein expression level of the at least one protein measured in step b) to the protein expression level of the at least one protein in a control sample, wherein a modulated protein expression level of the at least one protein measured in step b) compared to the protein expression level of the at least one protein in the control sample is indicative for UBE3A protein expression modulation.

In an embodiment of the method of the present invention, the protein expression level of the protein measured in step b) inversely correlates to the UBE3A protein expression level.

In a particular embodiment the method relates to a method for measuring UBE3A protein expression induction in a tissue sample comprising the steps:
a) providing a tissue sample of an animal or cell culture which has been treated with a UBE3A inducer,
b) measuring a protein expression level in the sample of step a) of at least one protein selected from the group consisting of: CCDC88A, DST, FAM127A, FAM127B, FAM127C, PEG10, TCAF1 and PPID.
c) comparing the protein expression level of the at least one protein measured in step b) to the protein expression level of the at least one protein in a control, wherein a decreased protein expression level of the at least one protein measured in step b) compared to the protein expression level of the at least one protein in the control is indicative for UBE3A protein expression induction.

In a particular embodiment the method relates to a method for determining UBE3A target engagement of an UBE3A modulator comprising the steps:
a) providing a tissue sample of an animal or cell culture which has been treated with a UBE3A modulator,
b) measuring a protein expression level in the sample of step a) of at least one protein selected from the group consisting of: CCDC88A, DST, FAM127A, FAM127B, FAM127C, PEG10, TCAF and PPID.
c) comparing the protein expression level of the at least one protein measured in step b) to the protein expression level of the at least one protein in a control, wherein a modulated protein expression level of the at least one protein measured in step b) compared to the protein expression level of the at least one protein in the control is indicative for UBE3A target engagement of the UBE3A modulator.

In a particular embodiment, the protein is selected from TCAF1 and PEG10.

In a particular embodiment, the tissue sample is a blood sample, a plasma sample or a CSF sample.

In a particular embodiment, the protein expression level is measured using Western blotting, MS or Immunoassays.

In a particular embodiment, the UBE3A modulator is an antisense oligonucleotide, in particular a LNA antisense oligonucleotide.

In a particular embodiment, the UBE3A modulator is an UBE3A protein expression level inducer for the treatment of Autism Spectrum Disorder, Angelman Syndrome or 15qdup syndrome.

In a second aspect the present invention relates to a screening method for the identification of UBE3A protein expression modulators comprising the steps:
a) providing a tissue sample of an animal or cell culture which has been treated with a test compound,
b) measuring a protein expression level in the sample of step a) of at least one protein selected from the group consisting of: CCDC88A, DST, FAM127A, FAM127B, FAM127C, PEG10, TCAF1 and PPID.
c) comparing the protein expression level of the at least one protein measured in step b) to the protein expression level of the at least one protein in a control, wherein a modulated protein expression level of the at least one protein measured in step b) compared to the protein expression level of the at least one protein in the control is indicative for a UBE3A protein expression modulator.

In a third aspect, the present invention relates to a use of a protein selected from the group consisting of CCDC88A, DST, FAM127A, FAM127B, FAM127C, PEG10, TCAF1 and PPID as biomarker for UBE3A protein expression level modulation.

In a particular embodiment of the use of the present invention, the protein is selected from TCAF1 and PEG10.

In a particular embodiment of the use of the present invention, the UBE3A modulation is due to a UBE3A protein expression level inducer.

In a particular embodiment of the use of the present invention, the protein expression level of the UBE3A biomarker inversely correlates to the UBE3A protein expression level.

In a particular embodiment of the use of the present invention, the present invention provides a method for determining UBE3A target engagement of an UBE3A protein expression level modulator.

In a particular embodiment of the use of the present invention, the UBE3A protein expression level modulator is an antisense oligonucleotide, in particular a LNA antisense oligonucleotide.

In a particular embodiment of the use of the present invention, the UBE3A protein expression level modulator is an UBE3A protein expression level inducer for the treatment of Autism Spectrum Disorder, Angelman Syndrome or 15qdup syndrome.

Definitions

The term "protein," as used herein, refers to any native protein from any vertebrate source, including mammals such as primates (e.g. humans) and rodents (e.g., mice and rats), unless otherwise indicated. The term encompasses "full-length," unprocessed proteins as well as any form of protein which results from processing in the cell as well as peptides derived from the native protein. The term also encompasses naturally occurring variants e.g., splice variants or allelic variants. The amino acid sequences shown in Table 2 are exemplary amino acid sequences of the biomarker proteins of the present invention.

In the present invention, an UBE3A protein expression level modulator refers to a molecule capable of reducing or enhancing the protein expression level of UBE3A. A modulator capable of reducing the protein expression level of UBE3A is referred to as UBE3A inhibitor and a modulator capable of enhancing the protein expression level of UBE3A is referred to as UBE3A enhancer. An UBE3A modulator may be an mRNA interfering RNA molecule. In another embodiment, the UBE3A modulator is a double-stranded RNA (dsRNA), for example, a short interfering RNA (siRNA) or a short hairpin RNA (shRNA). The double-stranded RNA may be any type of RNA, including but not limited to mRNA, snRNA, microRNA, and tRNA. RNA interference (RNAi) is particularly useful for specifically inhibiting the production of specific RNA and/or proteins. The design and production of dsRNA molecules suitable for the present invention are within the skill of those skilled in the art, particularly with reference to WO 99/32619, WO 99/53050, WO 99/49029 and WO 01/34815. Preferably siRNA molecule comprises a nucleotide sequence having about 19 to 23 contiguous nucleotides identical to the target mRNA. The term "shRNA" refers to a siRNA molecule in which fewer than about 50 nucleotides pair with the complementary sequence on the same RNA molecule, which sequence and complementary sequence are separated by an unpaired region of at least about 4 to 15 nucleotides (forming a single-chain loop on the stem structure produced by the two base-complementary regions). There are well-established siRNA design criteria (see, for example, Elbashire et al., 2001).

The UBE3A modulator can be an antisense oligonucleotide which is capable of modulating expression of a target gene by hybridizing to a target nucleic acid, in particular to a contiguous sequence on a target nucleic acid. The antisense oligonucleotides are not essentially double stranded and are therefore not siRNAs or shRNAs. Preferably, the antisense oligonucleotides are single stranded. It is understood that single stranded oligonucleotides can form hairpins or intermolecular duplex structures (duplex between two molecules of the same oligonucleotide), as long as the degree of intra or inter self-complementarity is less than 50% across of the full length of the oligonucleotide.

The term "control sample" refers to a sample which has not been treated with a UBE3A modulator. For example, the control sample is a sample of a cell culture which has not been treated with a UBE3A modulator or the cell culture has been treated with a compound which is not a UBE3A modulator (negative control).

Results

Protein profiling was performed on AS patient and healthy control human induced pluripotent stem cell (iPSC)-derived neurons. UBE3A and proteins and pathways were deregulated across patient lines. Using ASOs, reducing UBE3A protein in control lines or restoring it in patient lines, by knocking down the sense or anti-sense transcript respectively, reciprocally modulated a subset of these proteins. These UBE3A dependent proteins include CCDC88A, DST, FAM127A, FAM127B, FAM127C, PEG10, PPID and TCAF1. FAM127A, FAM127B, FAM127C, PEG10 are LTR of LTR retrotransposon-derived genes containing GAG capsid domains which may have function in exosomal physiology.

FIG. 1. Identification of novel Ube3a targets including proteins CCDC88A, DST, FAM127A, FAM127B, FAM127C, PEG10, PPID and TCAF1

In order to identify proteins that are modulated in response to changes in Ube3a protein levels, we performed Ube3a knockdown in Control IPSC derived neurons and increased Ube3a expression in AS lines by knocking down Ube3a ATS targeting sequence. The cell pellets were further subjected to protein expression profiling using TMT-SPS-MS3 quantification. TMT-MS3 data was analyzed on proteome discoverer 2.1 and results table was further subjected to statistical analysis to obtain proteins that are modulated upon changes on Ube3a levels by filtering for proteins that get upregulated upon Ube3a knockdown in Control neurons and the ones that get downregulated upon reinstatement of Ube3a in AS cells (FIG. 1).

FIG. 2: Confirmation of PEG 10 and TCAF1 as UBE3A target by SRM

A selective reaction monitoring (SRM) assay (Dunkley et al) was setup for the shortlisted proteins, CCDC88A, DST, HERC2, UCHL5, HERC1, MCF2L, PEG10, TCAF1, UBE3A was setup using unique peptides (At least one peptide for each protein) mapping to each of these proteins. SRM was performed using two Control lines and 3 AS lines following the same treatment as earlier (Ube3a knockdown in Control cells and Ube3a Reinstatement in AS cells). FIG. 2 shows bar charts for UBE3A, PEG10, TCAF1 showing an inverse modulation with respect to changes in UBE3A levels.

FIG. 3: Confirmation of PEG 10 and TCAF1 as UBE3A targets by WB

In order to determine if PEG10 showed any isoform specificity with respect to regulation by UBE3A, we performed western blotting for PEG10 and UBE3A in control and AS cells. PEG10 isoform RF1/2 was observed to be most dramatically regulated in a UBE3A dependent manner while PEG10 RF 1 largely remained unchanged upon changes in UBE3A levels (FIG. 3).

FIG. 4: Demonstration that PEG10 is regulated by UBE3A using immunocytochemistry FIG. 4A: Using an antibody that specifically recognizes RF1/2 we confirmed PEG10 expression to be neuron specific (co-localized with HuCD), elevated upon UBE3A knockdown, elevated in AS neurons and rescued with UBE3A reinstatement. PEG10 RF1/2 shows largely diffused staining in neuronal soma.

FIG. 4B: Quantification of PEG10 intensities in Control and AS HuCD positive neurons in Control and AS neurons (data points are individual neurons from two independent neuronal differentiations of control and AS cells, P values are adjusted for multiple comparisons based on Dunn's multiple comparison test).

FIG. 5: Demonstration that PEG10 and UBE3A can form a protein complex and PEG10 is regulated by UBE3A in an Ubiquitination dependent manner.

To assess if PEG10's overexpression upon UBE3A down-regulation was proteasome dependent, we performed immunoblotting for PEG10 under increasing duration of proteasome inhibition (MG132) in control neurons and upon UBE3A knockdown (sense) (FIG. 5A). Immunoblotting with Anti-K48 Ub revealed a robust increase in poly-ubiquitinated proteins with MG132 treatment (FIG. 5A, top). MG132 treatment did not significantly alter UBE3A expression within 8 hr of MG132 treatment. As expected, PEG10 RF1/2 expression increased with UBE3A knockdown. With 4 and 8 hr of MG132, we observed a robust increase in PEG10 RF1/2 expression, while no significant increase in PEG10 RF1/2 was observed under UBE3A knockdown (FIG. 5A, right quantified). We next performed Immunoprecipiatation for UBE3A in control, AS and AS with UBE3A reinstated (AS+ATS) cells under normal (DMSO) or MG132 treatment followed by western blotting for UBE3A and PEG10. We saw no PEG10 enrichment for UBE3A in control cells, while residual UBE3A in AS cells revealed binding to PEG10, which was diminished with the ATS treatment. Under proteasome inhibition, we observed an enrichment of PEG10-UBE3A complexes under all conditions (FIG. 5B, red astrix). Correspondingly, PEG10 IP-WB reveled PEG10 poly-ubiquitination smear in Control neurons upon MG132 treatment, which was diminished in AS neurons despite high PEG10 levels and was rescued with UBE3A rescue (ATS LNA) (FIG. 5C).

FIG. 6: PEG10 is secreted in extracellular vesicles from Angelman neurons.

To test if like with viruses, PEG10 can also be secreted in extracellular vesicles (EVs), we isolated extracellular vesicles from control and AS neurons (FIG. 6A). FIG. 6B: Using immunoelectron microscopy (immuno-EM), we confirmed the presence of canonical EV marker TSG101 and PEG10 RF1/2 in EVs from AS neurons. FIG. 6C: Quantification of EVs from Control and AS neurons using immuno-EM revealed that 20.73 (±1.27 s.e.m) percent of AS EVs were positive for PEG10, as opposed to 6.26 (±1.68 s.e.m) in controls. FIG. 6D: Next we performed data independent acquisition (DIA) mass spectrometry on control and AS cell lysates and the corresponding EV fractions. DIA analysis confirmed significant up-regulation of PEG10 in AS cell lysates and EVs (Log 2 FC=0.99 and 0.80, Adj. P=0), while PEG10 was not enriched in EVs preferentially over lysates like core EV makers (TSG101, Alix, CD81 and CD63). Of the proteins confirmed to be PEG10 binding partners, TCAF1 was elevated in AS lysates and EVs and ATXN10 was selectively elevated in EVs from AS neurons while RTL8C showed elevation in AS lysates, but not in EVs. FIG. 6E: We next confirmed the expression and enrichment of PEG10 RF1/2 in EVs using WB. PEG10 RF1/2 is secreted in EVs and shows fragmentation in EVs. In agreement with DIA results, TSG101 and Alix (PDCD6IP), were enriched in EVs, while ATXN10 was selectively enriched in AS EVs. Thus, PEG10 recruits its binding partners ATXN10, TCAF1 and FAM127A/RTL8C into EVs.

Materials and Methods

NSCs obtained from IPSCs were differentiated into neurons as per Costa et al, 2016.

LNA Treatment and Sample Preparation for TMT-MS3-SPS Analysis:

Neurons obtained from control samples were treated with 1 and 5 M UBE3A sense sequence targeting LNA 5'-TT-TAcacctacttcttaaCA-3' (Seq. Id. No. 35) and AS cells were treated with UBE3A Antisense targeting sequence 5'-CTttc-catttatttccATTT-3' (Seq. Id. No. 36) based on patent (WO2017081223A1). Cells at day 42 of neuronal differentiation were collected and subjected to sample preparation according to Gygi paper. Conditions were randomized into 6 TMTx10 plex runs with each TMTx10 plex run containing 2 pooled samples. Post labeling, the samples were pooled and subjected to basic reverse phase fractionation on a Agilent 1260 infinity series HPLC (Agilent Technologies, Waldbronn, Germany) on a YMC-Triart C18 Column (0.5 mm×250 mm, S-3 µm particle size, 12 nm pore size). Fractionation of the samples was performed using the following gradient at 12 µl/min. 2-23% buffer B for 5 minutes, 23-33% buffer B for 25 minutes, 33-53% buffer B for 30 minutes, 53-100% buffer B for 5 minutes and 100% buffer B for 5 minutes. The column is equilibrated by changing from 100% buffer B to 2% buffer B in 1 minute followed by 2% buffer B for 14 minutes. A total of 36 fractions are collected in a 96 well sample plate from 4 minutes to 84 minutes consisting of ~26 µl volume each.

Following fractionation, the samples were dried, acidified and the data was acquired on a ORBITRAP FUSION™ LUMOS™ TRIBRID™ (Thermo Fisher Scientific) mass spectrometer. The instrument is operated in data-dependent acquisition mode to collect Orbitrap MS1 scans over a mass range of 350-1400 m/z at a resolution of 120,000 (at m/z 200) with an automatic gain control (AGC) target value of 2E5 with maximum injection time (IT) of 50 ms. Data was calibrated on the fly using ambient air hexacyclodimethylsiloxane at m/z 445.12002. Between each MS1 scan, for a period of 3 seconds, the N most intense precursor ions with charge states between 2-6, with a minimum intensity of 5E3, were mono-isotopically selected for collision induced dissociation (CID), using a quadrupole isolation of m/z 0.7, AGC target 1E4, maximum IT 50 ms, collision energy of 35%, and ion trap readout with turbo scan rate. Precursor ions are excluded after 1 appearance for 75 seconds using 10 ppm as low and high mass tolerance. The dependent scan was performed on a single charge state per precursor. TMT reporter ions are generated using synchronous precursor selection (SPS), an MS quadrupole isolation window of m/z 2, high-energy collision dissociation (HCD) at a normalized collision energy of 65%, and readout in the Orbitrap with a resolution of 50 k (at m/z 200), scan range of m/z 100 to 500, an AGC target of 5E4, and a maximum IT of 105 ms. The mass range for selecting the SPS precursors was from m/z 400 to 2000, excluding the MS2 precursor with a tolerance of m/z 40 (low) and 5 (high), and any TMT neutral loss from it. The number of SPS precursors is set to 10.

Data Analysis on Proteome Discoverer:
1. Post acquisition, the raw data was processed using Proteome Discoverer 2.1 connected to MASCOT® Server 2.6.1 (Matrix Science, London, UK).
2. The processing workflow searches the $MS^2$ data against the UniProt human protein database using trypsin/P as an enzyme, allowing for a maximum of 2 missed cleavages and 10 ppm and 0.5 Da precursor and fragment ion tolerances, respectively.
3. Carbamidomethylated cysteine (+57.02146 Da), TMT10 labeled lysine and peptide N-terminus (+229.16293 Da) are set as static modifications.
4. Oxidized methionine (+15.99492 Da) and acetylated protein N-terminus (+42.01057 Da) are set as dynamic modifications.
5. A decoy database search was performed using Percolator with the Target FDR set to 0.01 based on q-value threshold.
6. Reporter ion quantification was performed on the $HCD-MS^3$ data, with 3 mmu peak integration and using the most confident centroid tolerances.
7. Reporter ion intensities are adjusted so as to correct for the isotope impurities of different TMT reagents using the manufacturer specifications.
8. A consensus workflow was defined to group PSMs into peptide and proteins.
9. Peptide FDRs are controlled by setting a q-value threshold of 0.01 and allowing the software to automatically select PSM q-value for the grouping.
10. High confidence unique peptides with a minimal length of 6 amino acids are grouped into proteins and protein FDR was also set to 0.01.
11. Peptide and protein quantification was done by summing the S/N for each channel and normalizing each value with the highest TMT channel total intensity. Individual peptide and protein S/N are scaled to an average of 100 and only high FDR confidence protein quantification intensities are kept for statistical analysis.

Statistical Analysis:

Samples were analyzed in 6 10-plex TMT runs with two pooled samples in each plex. Data were annotated and normalized with Proteome Discoverer (version 2.1, Thermo Fisher Scientific). Normalization was done on the peptide level to the maximum of summed intensities for each channel. The common pooled samples were used to normalize across the 6 TMT-plexes with the IRS method: scaling factors were calculated for each protein to adjust their reference value to the geometric mean of the pooled samples. These were then used to scale the abundances for each protein in the remaining samples in each TMT experiment as per Plubell et al, 2017. Differential abundances of proteins were calculated using limma (Ritchie et al, 2015) by fitting linear models for each protein, and applying an Empirical Bayes method to moderate the variances (Phipson et al, 2016). Different conditions were compared by calculating contrasts with multcomp (Hothorn et al, 2008) and lsmeans (Russel and Length et al 2016). The computed p-values were adjusted for multiple testing by controlling the false discovery rate (Benjamini, and Hochberg 1995). All calculations were performed in R (R Core team, 2018).

Selective Reaction Monitoring (SRM) of UBE3A Targets

Isotope-labeled peptides (unpurified), containing either L-[U-13C, U-15N]R or L-[U-13C, U-15N]K, corresponding to the 26 target peptides as shown in Table 1 were synthesized (JPT Peptide Technologies) and their sequences confirmed by LC-MS/MS. Cell pellets from two control and three AS neurons were subjected to LNA treatments in 3 independent differentiations were subjected to in solution digestion using the Preomics kit (Preomics GmBH). 50 fmol of the pooled peptide mix was spiked in each sample and measured and analyzed on Q-Exactive Mass spectrometer (Thermo) according to Dunkley et al, 2015. Data was processed on Skyline and endogenous peptide abundances corrected using the heavy reference standards, normalized for ACTB. FIG. 2 represents abundances of selected proteins, PEG10, TCAF1 and UBE3A.

TABLE 1

Synthetic peptides used for SRM assay for UBE3A and validating UBE3A targets.

| GENE | Peptide Sequence | Seq. Id. No. |
|------|------------------|--------------|
| UBE3A | VDPLETELGVK | 9 |
| UCHL5 | WQPGEEPAGSVVQDSR | 10 |
| UCHL5 | EFSQSFDAAMK | 11 |
| TCAF1 | TLENPEPLLR | 12 |
| TCAF1 | LGAEPFPLR | 13 |
| TCAF1 | EVATSLAYLPEWK | 14 |
| PPID | HVVFGQVIK | 15 |
| PPID | NIGNTFFK | 16 |
| MCF2L | TAIESFALMVK | 17 |
| MCF2L | MEDFQIYEK | 18 |
| MCF2L | EEVYIVQAPTPEIK | 19 |
| HERC2 | INEPGQSAVFCGR | 20 |
| HERC2 | FTVYPIMPAAGPK | 21 |
| DST | ENTAYFEFFNDAK | 22 |
| DST | VLQEDILLR | 23 |
| DST | SEAYQQQIEMER | 24 |
| DST | EVIPQEIEEVK | 25 |
| DST | VGGGWMALDEFLVK | 26 |
| CCDC88A | SLGHEVNELTSSR | 27 |
| CCDC88A | SLEQETSQLEK | 28 |
| CCDC88A | ASSVISTAEGTTR | 29 |
| ACTB | GYSFTTTAER | 30 |
| ACTB | EITALAPSTMK | 31 |
| PEG10 | EQVEPTPEDEDDDIELR | 32 |
| PEG10 | WLSTHDPNITWSTR | 33 |
| PEG10 | SIVFDSEYCR | 34 |

Western Blotting for PEG10 and UBE3A.

For western blotting on neuronal cell pellets denatured in RIPA buffer (Thermo Fisher Scientific, Cat no. 89900) by incubation with RIPA lysis buffer for 20 min at 4° C., sonicated and subjected to reduction (10× NuPAGE™ Sample Reducing Agent, Thermo Fisher Scientific, Cat. no. NP0004) and denaturation using 4× Laemmli sample lysis buffer (Biorad, Cat. No. 1610747) following boiling at 95° C.

Samples were separated on a 4-15% Criterion™ TGX Stain-Free™ Precast Gels (Biorad, Cat no. 5678084), subjected to wet transfer using Biorad wet transfer using Criterion™ Blotter onto PVDF membranes. Post transfer, the PVDF membranes were blocked using 5% milk in Tris buffer saline −0.1% TWEEN® 20 (TBS-T) and incubated with UBE3A (E6AP Antibody, A300-352A—Bethyl Laboratories)/PEG10 (Anti-PEG10 antibody [1E2-F12-C12] (ab131194)| Abcam) Antibodies at 1:500 dilution and detected using HRP conjugated secondary antibodies (DAKO) using a Gel Doc™ XR+ (Biorad) system.

TABLE 2

Biomarker proteins of the present invention

| Human Protein | REFSEQ reference | Uniprot ID | Seq. Id. No. |
|---------------|------------------|------------|--------------|
| CCDC88A | AAI44321/ NP_001129069.1 | Q3V6T2 | 1 |
| DST | AAH65536/NP_899236.1 | Q03001 | 2 |
| FAM127A | /NP_001071639.1 | A6ZKI3 | 3 |
| FAM127B | NP_001071640.1 | Q9BWD3 | 4 |
| FAM127C | NP_001071641.1 | Q17RB0 | 5 |
| PEG10 | NP_055883.2 | Q86TG7 | 6 |
| TCAF1 | NP_055534 | Q9Y4C2 | 7 |
| PPID | NP_005029.1 | Q08752 | 8 |

REFERENCES

R Core Team (2018). R: A language and environment for statistical computing. R Foundation for Statistical Computing, Vienna, Austria. https://www.R-project.org/.

Plubell, D. L., Wilmarth, P. A., Zhao, Y., Fenton, A. M., Minnier, J., Reddy, A. P., Klimek, J., Yang, X., David, L. L., . . . Pamir, N. (2017). Extended Multiplexing of Tandem Mass Tags (TMT) Labeling Reveals Age and High Fat Diet Specific Proteome Changes in Mouse Epididymal Adipose Tissue. Molecular & cellular proteomics 16(5), 873-890.

Ritchie, M. E., Phipson, B., Wu, D., Hu, Y., Law, C. W., Shi, W., and Smyth, G. K. (2015). limma powers differential expression analyses for RNA-sequencing and microarray studies. Nucleic Acids Research 43(7), e47.

Phipson, B, Lee, S, Majewski, IJ, Alexander, W S, and Smyth, G K (2016). Robust hyperparameter estimation protects against hypervariable genes and improves power to detect differential expression. Annals of Applied Statistics 10(2), 946-963.

Torsten Hothorn, Frank Bretz and Peter Westfall (2008). Simultaneous Inference in General Parametric Models. Biometrical Journal 50(3), 346-363.

Russell V. Lenth (2016). Least-Squares Means: The R Package lsmeans. Journal of Statistical Software 69(1), 1-33.

Benjamini, Y., and Hochberg, Y. (1995). Controlling the false discovery rate: a practical and powerful approach to multiple testing. Journal of the Royal Statistical Society Series B 57, 289-300.

S. M. Elbashir, W. Lendeckel, and T. Tuschl, "RNA interference is mediated by 21- and 22-nucleotide RNAs," Genes Dev., vol. 15, no. 2, pp. 188-200, 2001.

V. Costa, S. Aigner, M. Vukcevic, E. Sauter, K. Behr, M. Ebeling, T. Dunkley, A. Friedlein, S. Zoffmann, C. A. Meyer, F. Knoflach, S. Lugert, C. Patsch, F. Fjeldskaar, L. Chicha-Gaudimier, A. Kiialainen, P. Piraino, M. Bedoucha, M. Graf, S. Jessberger, A. Ghosh, J. Bischofberger, and R. Jagasia, "MTORC1 Inhibition Corrects Neurodevelopmental and Synaptic Alterations in a Human Stem Cell Model of Tuberous Sclerosis," Cell Rep., vol. 15, no. 1, pp. 86-95, 2016.

T. Dunkley, V. Costa, A. Friedlein, S. Lugert, S. Aigner, M. Ebeling, M. T. Miller, C. Patsch, P. Piraino, P. Cutler, and R. Jagasia, "Characterization of a human pluripotent stem cell-derived model of neuronal development using multiplexed targeted proteomics," Proteomics—Clin. Appl., vol. 9, no. 7-8, pp. 684-694, 2015.

The invention claimed is:

1. A method for measuring UBE3A protein expression modulation in a cerebral spinal fluid (CSF) sample comprising the steps:
   a) providing a CSF sample of an animal which has been treated with a UBE3A modulator comprising an antisense oligonucleotide,
   b) measuring a protein expression level in the sample of step a) of at least one protein selected from the group consisting of: CCDC88A, DST, FAM127A, FAM127B, FAM127C, PEG10, TCAF1, and PPID,
   c) comparing the protein expression level of the at least one protein measured in step b) to the protein expression level of the at least one protein in a control, wherein a modulated protein expression level of the at least one protein measured in step b) compared to the protein expression level of the at least one protein in the control is indicative for UBE3A protein expression modulation.

2. The method of claim 1, wherein the protein expression level of the protein measured in step b) inversely correlates to the UBE3A protein expression level.

3. The method of claim 1, wherein the protein is selected from TCAF1 and PEG10.

4. The method of claim 1, wherein the protein expression level is measured using Western blotting, MS or Immunoassay.

5. The method of claim 1, wherein the UBE3A modulator is a LNA antisense oligonucleotide.

6. A method for measuring UBE3A protein expression induction in a CSF sample comprising the steps:
   a) providing a CSF sample of an animal which has been treated with a UBE3A inducer comprising an antisense oligonucleotide,
   b) measuring a protein expression level in the sample of step a) of at least one protein selected from the group consisting of: CCDC88A, DST, FAM127A, FAM127B, FAM127C, PEG10, TCAF1 and PPID,
   c) comparing the protein expression level of the at least one protein measured in step b) to the protein expression level of the at least one protein in a control, wherein a decreased protein expression level of the at least one protein measured in step b) compared to the protein expression level of the at least one protein in the control is indicative for UBE3A protein expression induction.

7. The method of 6, wherein the antisense oligonucleotide is a LNA antisense oligonucleotide.

8. The method of claim 6, wherein the protein is selected from TCAF1 and PEG10.

9. A method for determining UBE3A target engagement of an UBE3A modulator comprising the steps:
   a) providing a CSF sample of an animal which has been treated with a UBE3A modulator comprising an antisense oligonucleotide,
   b) measuring a protein expression level in the sample of step a) of at least one protein selected from the group consisting of: CCDC88A, DST, FAM127A, FAM127B, FAM127C, PEG10, TCAF1 and PPID,
   c) comparing the protein expression level of the at least one protein measured in step b) to the protein expression level of the at least one protein in a control, wherein a modulated protein expression level of the at least one protein measured in step b) compared to the protein expression level of the at least one protein in the control is indicative for UBE3A target engagement of the UBE3A modulator.

10. The method of 9, wherein the antisense oligonucleotide is a LNA antisense oligonucleotide.

11. The method of claim 9, wherein the protein is selected from TCAF1 and PEG10.

12. A screening method for the identification of UBE3A protein expression modulators comprising the steps:
- a) providing a CSF sample of an animal which has been treated with a test compound comprising an antisense oligonucleotide,
- b) measuring a protein expression level in the sample of step a) of at least one protein selected from the group consisting of: CCDC88A, DST, FAM127A, FAM127B, FAM127C, PEG10, TCAF1 and PPID,
- c) comparing the protein expression level of the at least one protein measured in step b) to the protein expression level of the at least one protein in a control, wherein a modulated protein expression level of the at least one protein measured in step b) compared to the protein expression level of the at least one protein in the control is indicative for a UBE3A protein expression modulator.

13. The method of claim 12, wherein the protein is selected from TCAF1 and PEG10.

14. The method of claim 12, wherein the protein expression level of the UBE3A biomarker inversely correlates to the UBE3A protein expression level.

15. The method of claim 12, wherein the antisense oligonucleotide is a LNA antisense oligonucleotide.

\* \* \* \* \*